(12) United States Patent
Cai

(10) Patent No.: US 12,274,565 B2
(45) Date of Patent: Apr. 15, 2025

(54) BIOLOGICAL CHARACTERISTIC INFORMATION DETECTION DEVICE AND ELECTRONIC DEVICE

(71) Applicant: SHENZHEN GOODIX TECHNOLOGY CO., LTD., Guangdong (CN)

(72) Inventor: Jun Cai, Guangdong (CN)

(73) Assignee: SHENZHEN GOODIX TECHNOLOGY CO., LTD., Guangdong (CN)

( * ) Notice: Subject to any disclaimer, the term of this patent is extended or adjusted under 35 U.S.C. 154(b) by 841 days.

(21) Appl. No.: 17/512,072

(22) Filed: Oct. 27, 2021

(65) Prior Publication Data
US 2022/0175321 A1 Jun. 9, 2022

Related U.S. Application Data

(63) Continuation of application No. PCT/CN2020/135013, filed on Dec. 9, 2020.

(51) Int. Cl.
*A61B 5/00* (2006.01)
*A61B 5/021* (2006.01)
(Continued)

(52) U.S. Cl.
CPC ........ *A61B 5/6898* (2013.01); *A61B 5/02108* (2013.01); *A61B 5/02416* (2013.01); *A61B 5/282* (2021.01); *A61B 5/318* (2021.01); *A61B 2560/0223* (2013.01); *A61B 2562/0247* (2013.01)

(58) Field of Classification Search
None
See application file for complete search history.

(56) References Cited

U.S. PATENT DOCUMENTS 8,761,853 B2 6/2014 Thaveeprungsriporn et al.
9,072,439 B2 7/2015 Kassim et al.
(Continued)

FOREIGN PATENT DOCUMENTS

CN 103228205 A 7/2013
CN 204520705 U 8/2015
(Continued)

*Primary Examiner* — Yi-Shan Yang
(74) *Attorney, Agent, or Firm* — Scully, Scott, Murphy & Presser, P.C.

(57) ABSTRACT

Disclosed are a detection apparatus for biological characteristic information and an electronic device. The detection apparatus including a first button. A cavity is formed in a shell of the first button. The detection apparatus includes: a first detection part. The first detection part includes: a first pulse wave detection module at least partially arranged in the cavity and configured to detect a first pulse wave signal of a user when the user presses the first button; and a pressure sensing module at least partially arranged in the cavity of the first button and configured to detect a pressure signal applied to the first button by the user, where the first pulse wave signal is a corresponding pulse wave signal when the user applies the pressure signal, and the pressure signal and the first pulse wave signal are used to detect first biological characteristic information of the user.

16 Claims, 12 Drawing Sheets

(51) Int. Cl.
*A61B 5/024* (2006.01)
*A61B 5/282* (2021.01)
*A61B 5/318* (2021.01)

(56) References Cited

U.S. PATENT DOCUMENTS

| | | |
|---|---|---|
| 9,480,407 B2 | 11/2016 | Kumar et al. |
| 9,538,927 B2 | 1/2017 | Thaveeprungsriporn et al. |
| 2012/0190944 A1 | 7/2012 | Thaveeprungsriporn et al. |
| 2013/0296665 A1 | 11/2013 | Kassim et al. |
| 2013/0296666 A1 | 11/2013 | Kumar et al. |
| 2013/0296673 A1 | 11/2013 | Thaveeprungsriporn et al. |
| 2013/0296714 A1 | 11/2013 | Kassim et al. |
| 2014/0364749 A1 | 12/2014 | Varma et al. |
| 2016/0378965 A1* | 12/2016 | Choe ............... G06F 1/1626 726/19 |
| 2017/0119307 A1 | 5/2017 | Shim et al. |
| 2017/0188953 A1* | 7/2017 | Jeon ............... A61B 5/14552 |
| 2017/0360374 A1 | 12/2017 | Elliott et al. |
| 2018/0055381 A1* | 3/2018 | Segman ............... A61B 8/5223 |
| 2018/0317784 A1* | 11/2018 | Albert ............... A61B 5/02125 |
| 2018/0317857 A1 | 11/2018 | Segman |
| 2018/0325397 A1 | 11/2018 | Presura et al. |
| 2018/0344193 A1 | 12/2018 | Gui et al. |
| 2019/0021606 A1* | 1/2019 | Martin ............... A61B 5/332 |
| 2019/0365255 A1 | 12/2019 | Kitagawa et al. |
| 2020/0163561 A1 | 5/2020 | Choe |
| 2020/0196881 A1 | 6/2020 | Zemel |
| 2020/0383641 A1* | 12/2020 | Hwang ............... A61B 5/7278 |
| 2021/0321884 A1* | 10/2021 | Hwang ............... G06V 40/1376 |
| 2021/0386305 A1* | 12/2021 | Kwon ............... A61B 5/6843 |

FOREIGN PATENT DOCUMENTS

| | | |
|---|---|---|
| CN | 105686818 A | 6/2016 |
| CN | 205568938 U | 9/2016 |
| CN | 205697733 U | 11/2016 |
| CN | 108430317 A | 8/2018 |
| CN | 207855679 U | 9/2018 |
| CN | 109965862 A | 7/2019 |
| CN | 111194181 A | 5/2020 |
| CN | 212539480 U | 2/2021 |
| CN | 113080913 A | 7/2021 |
| GB | 2578120 A | 4/2020 |
| JP | 2014507209 A | 3/2014 |
| JP | WO2015151132 A1 | 4/2017 |
| KR | 20170049280 A | 5/2017 |
| WO | 2019051108 A1 | 3/2019 |

* cited by examiner

BIOLOGICAL CHARACTERISTIC INFORMATION DETECTION DEVICE AND ELECTRONIC DEVICE

CROSS-REFERENCE TO RELATED APPLICATIONS

This application is a continuation of International Application No. PCT/CN2020/135013, filed on Dec. 9, 2020, the disclosure of which is hereby incorporated by reference in its entirety.

TECHNICAL FIELD

The present application relates to a detection apparatus for biological characteristic information and an electronic device.

BACKGROUND

In recent years, with the rapid development of electronic technology, how to monitor biological characteristic information of a human body in real time so as to make users know their own body conditions at any time and play a role in preventing diseases has attracted widespread attention.

For example, blood pressure, as the biological characteristic information for measuring human cardiovascular system, is of great significance in disease diagnosis, treatment process and prognosis judgment. At present, the portable blood pressure detection apparatus in the market generally determine the blood pressure value based on pulse wave, but the detection of pulse wave is restricted by many environmental factors, so the measurement accuracy is low.

Therefore, a detection apparatus for biological characteristic information with portability and high accuracy is provided, which has a great application prospect and market value.

SUMMARY

An embodiment of the present application provides a detection apparatus for biological characteristic information and an electronic device, where biological characteristic information detected by the detection apparatus has high accuracy, and the detection apparatus is convenient to carry.

According to a first aspect, a detection apparatus for biological characteristic information is provided. The detection apparatus is applied to an electronic device which includes a first button. A cavity is formed in a shell of the first button. The detection apparatus includes: a first detection part. The first detection part includes: a first pulse wave detection module, at least partially arranged in the cavity of the first button and configured to detect a first pulse wave signal of a user when the user presses the first button; and a pressure sensing module, at least partially arranged in the cavity of the first button and configured to detect a pressure signal applied to the first button by the user, where the first pulse wave signal is a corresponding pulse wave signal when the user applies the pressure signal, and the pressure signal and the first pulse wave signal are used to detect first biological characteristic information of the user.

Through the technical solution of the embodiment of the present application, the first pulse wave detection module is configured to detect the first pulse wave signal when a user presses, where the first pulse wave signal is a pulse wave signal corresponding to a pressure signal pressed by the user; meanwhile, the pressure sensing module is configured to detect the pressure signal pressed by the user. Compared with the solution in the prior art that the biological characteristic information is detected by directly detecting the pulse wave signal without pressure and needs to be calibrated under the assistance of external devices such as a sphygmomanometer, the solution of detecting the biological characteristic information by combining the pressure signal and the first pulse wave signal can directly measure more accurate biological characteristic information according to the detection apparatus itself, so the detection apparatus has high accuracy of detecting biological characteristic information and is convenient to carry. Further, in the embodiment of the present application, the first pulse wave detection module and the pressure sensing module in the first detection part are at least partially arranged in the cavity of the first button of the electronic device, so that the user may rapidly find an operating part where the first detection part is located, it is convenient for the user to perform pressing operation on the button, the use experience of the user is improved, the volume of the electronic device can be reduced, and the appearance of the electronic device is not affected.

In some possible implementation manners, the pressure sensing module and the first pulse wave detection module are stacked, and the pressure sensing module is located on one side, facing towards the inside of the electronic device, of the first pulse wave detection module.

In some possible implementation manners, the first pulse wave detection module is fixedly connected to a shell of the first button, and the pressure sensing module is fixedly connected to the first pulse wave detection module. The first detection part further includes: a first structural component, arranged on one side, facing towards the inside of the electronic device, of the pressure sensing module; when the user presses the first button, the pressure sensing module and the first pulse wave detection module are configured to press the first structural component in a linkage way; and the pressure sensing module is configured to detect an action force between the pressure sensing module and the first structural component so as to detect the pressure signal applied to the first button by the user.

In some possible implementation manners, the first detection part further includes: an elastic module, arranged on one side, facing towards the inside of the electronic device, of the first structural component and connected to the first structural component; when the user presses the first button, the first structural component, the pressure sensing module and the first pulse wave detection module are configured to press the elastic module in a linkage way; and the elastic module is configured to limit a movable distance of the pressure sensing module within a preset range so as to limit a force applied by the user within a pressure range bearable by the pressure sensing module.

In some possible implementation manners, an elastic structural component of the first button is reused as the elastic module, and the elastic structural component of the first button is configured to limit a pressing travel of the first button.

In some possible implementation manners, the first pulse wave detection module is fixedly connected to a shell of the first button, and the pressure sensing module is separably connected to one side of the first pulse wave detection module. The first detection part further includes: a first structural component, fixedly connected to one side, facing towards the inside of the electronic device, of the first pulse wave detection module; when the user presses the first button, the second structural component and the first pulse wave detection module are configured to press the pressure sensing module in a linkage way; and the pressure sensing module is configured to detect an action force between the pressure sensing module and the second structural component so as to detect the pressure signal.

In some possible implementation manners, the pressure sensing module includes an elastic component and a strain gauge, where the strain gauge is arranged in a middle area of a surface of the elastic component; the second structural component is configured to press an edge area of the surface of the elastic component so as to deform the elastic component; and the strain gauge is configured to detect the deformation so as to detect the pressure signal.

In some possible implementation manners, the first pulse wave detection module is a first photo plethysmography (PPG) detection module; and the first PPG detection module includes: a light-transmitting cover, a first light source and a first light detector, where the light-transmitting cover is configured to receive pressing of the user; the first light source and the first light detector are arranged on one side, facing towards the inside of the electronic device, of the light-transmitting cover; the first light source is configured to transmit an optical signal of a target waveband to a pressing site of the user at the light-transmitting cover; and the first light detector is configured to receive an optical signal reflected and/or transmitted by the pressing site to form the first pulse wave signal.

In some possible implementation manners, part of the shell of the first button is reused as the light-transmitting cover.

In some possible implementation manners, the first PPG detection module further includes: a lens, arranged between the light-transmitting cover and the first light source and configured to converge optical signals of the first light source to the pressing site the computer the user.

In some possible implementation manners, the first PPG detection module further includes: a spacer, located between the first light source and the computer first light detector to prevent the optical signal transmitted by the first light source from directly entering the computer first light detector.

In some possible implementation manners, the first PPG detection module further includes: a substrate and a bracket, where the substrate is configured to support the first light source and the first light detector; and the bracket is arranged on a peripheral edge of the substrate and configured to support the light-transmitting cover.

In some possible implementation manners, the light-transmitting cover, the bracket and the substrate form a closed chamber.

In some possible implementation manners, part of the shell of the first button is reused as the bracket and/or the substrate.

In some possible implementation manners, the first PPG detection module includes: a plurality of the first light sources and a plurality of the first light detectors, where the plurality of the first light sources are configured to transmit optical signals of at least two different target wavebands.

In some possible implementation manners, the first button is arranged on a side or a back of the electronic device.

In some possible implementation manners, a function button of the electronic device is reused as the first button.

In some possible implementation manners, a power button or volume button on a side of the electronic device is reused as the first button.

In some possible implementation manners, the first biological characteristic information of the user includes a blood pressure of the user.

In some possible implementation manners, the detection apparatus further includes: a second detection part. The second detection part includes: a second pulse wave detection module, configured to detect a second pulse wave signal; and an electrocardiograph (ECG) detection module, configured to detect an ECG signal of the user, where the second pulse wave signal and the ECG signal are used to detect second biological characteristic information of the user; and the first biological characteristic information and the second biological characteristic information are used for being processed to obtain a target biological characteristic information of the user.

In some possible implementation manners, the second pulse wave detection module is a second photo plethysmography (PPG) detection module, and the second PPG detection module is arranged on a back of the electronic device. The ECG detection module includes: a plurality of ECG detection electrodes, where a first ECG detection electrode of the plurality of ECG detection electrodes is arranged on a back of the electronic device, and a second ECG detection electrode of the plurality of ECG detection electrodes is arranged on a side of the electronic device.

In some possible implementation manners, the first button is arranged on a first side of the electronic device, the second ECG detection electrode is arranged on a second side of the electronic device, and the first side and the second side are two opposite sides of the electronic device respectively.

In some possible implementation manners, the second ECG detection electrode is arranged in a second button on a side of the electronic device.

In some possible implementation manners, the detection apparatus further includes: a processor, connected to the first detection part and the second detection part, where the processor is configured to acquire the first biological characteristic information of the user, acquire the second biological characteristic information of the user, and process of the first biological characteristic information and the second biological characteristic information to obtain the target biological characteristic information of the user.

In some possible implementation manners, the first biological characteristic information includes blood pressure calibrating information, the second biological characteristic information includes an initial blood pressure of the user, and the target biological characteristic information of the user includes a target blood pressure of the user. The processor is configured to calibrate the initial blood pressure according to the blood pressure calibrating information and take the calibrated blood pressure as the target blood pressure of the user.

In some possible implementation manners, the processor is configured to: control a prompt module to output a prompt signal, the prompt signal being used to prompt the user to press the first button to form the pressure signal; control the first pulse wave detection module to detect the first pulse wave signal; control the pressure sensing module to detect the pressure signal; and receive the pressure signal and the first pulse wave signal and determine the blood pressure calibrating information according to the pressure signal and the first pulse wave signal.

In some possible implementation manners, the pressure signal is variable from large to small or from small to large with time.

In some possible implementation manners, the processor is configured to: control the second pulse wave detection module to detect the second pulse wave signal of the user; and receive the second pulse wave signal and process the second pulse wave signal by a pulse wave analysis method or a pulse wave transit time measurement method to obtain the initial blood pressure of the user.

In some possible implementation manners, the first pulse wave signal is variable with the magnitude of the pressure signal. The processor is configured to: sequence the first pulse wave signal according to the magnitude of the pressure signal to form an envelope signal of the first pulse wave signal; determine a first blood pressure of the user according to the envelope signal; and take the first blood pressure as the blood pressure calibrating information.

According to a second aspect, an electronic device is provided. The electronic device includes: a detection apparatus for biological characteristic information in the first aspect or any one of possible implementation manners in the first aspect.

In some possible implementation manners, the electronic device is a smartwatch or mobile phone.

DESCRIPTION OF THE EMBODIMENTS

The technical solutions in embodiments of the present application are described below with reference to the accompanying drawings.

Specifically, the present application is applicable to a biological information detection system. The biological information detection system may be applied to various types of electronic devices. The electronic device may be an intelligent wearable device, a mobile phone, a tablet computer, a mobile medical device and the like, where the intelligent wearable device may include at least one of the following devices: a watch, a bracelet, an anklet, a necklace, glasses or a head-mounted device; and the mobile medical device may include any one of the following devices: a blood glucose monitoring device, a heart rate monitoring device, a blood pressure measuring device, a body temperature measuring device and the like, which are not limited by the embodiment of the present application.

Figure 1:
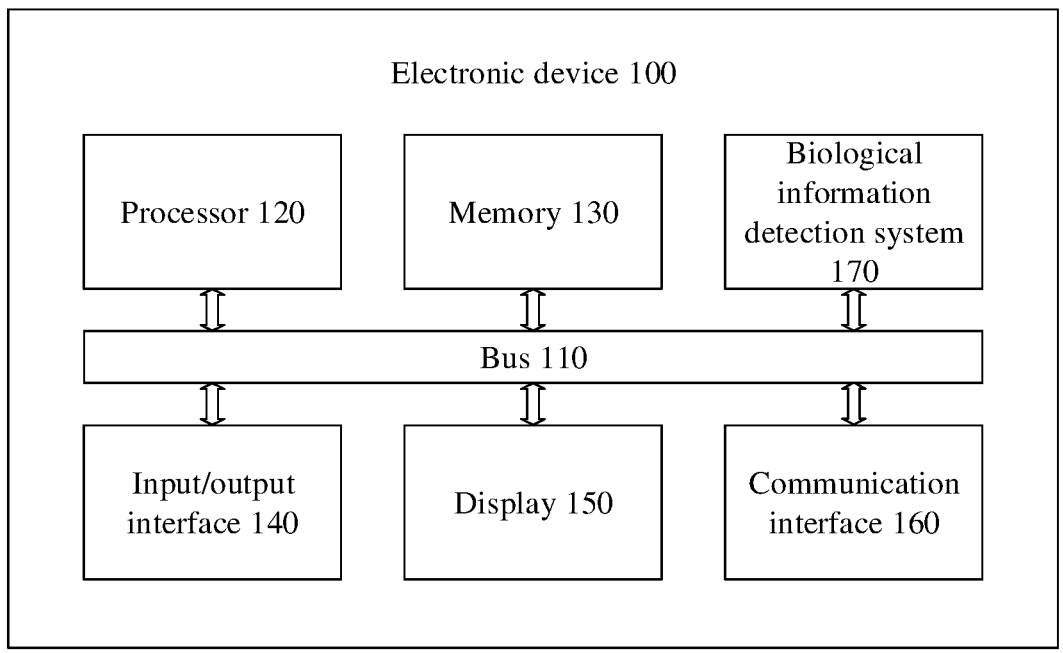
FIG. 1 is a structure block diagram of an electronic device suitable for a biological information detection system according to the present application.

FIG. 1 shows a structural block diagram of an electronic device suitable for a biological information system in the present application.

As shown in FIG. 1, the electronic device 100 may include a bus 110, a processor 120, a memory 130, an input/output interface 140, a display 150, a communication interface 160 and a biological information detection system 170.

The bus 110 may include a circuit for realizing transmission communication (for example, control messages or data) between various parts in the electronic device 100. The processor 120 may include one or more types of data processors for performing data processing. The memory 130 may include a volatile memory and/or a nonvolatile memory. The memory 130 may store instructions or data related to other function parts in the electronic device 100.

The input/output interface 140 may be configured to receive an instruction or data input from a user or an external device and then transmit the instruction or data to other function parts in the electronic device 100, or may output instructions or data generated by other function parts in the electronic device 100 to the user or the external device.

The display 150 may include, for example, a liquid crystal display (LCD), an organic light-emitting diode (OLED) or other types of displays. The display 150 may display various types of contents for users, for example, texts, images, videos, icons and the like. Further, the display 150 may include a touch screen, and a user may input related instruction information through the touch screen.

The communication interface 160 may be configured to realize communication between the electronic device 100 and an external device such as a network server or other electronic devices. As an example, the communication interface 160 may be connected to a communication network through wireless or wire communication and communicate with the external device. The wireless communication includes, but is not limited to cellular communication or short-distance communication. The wire communication includes, but is not limited to at least one of a universal serial bus (USB), a high definition multimedia interface (HDMI), recommended standard 232 (RS-232) or other communication modes.

The biological information detection system 170 is configured to detect biological characteristic information of a user, where the biological characteristic information includes, but is not limited to: parameter information such as heart rate, oxyhemoglobin saturation, blood pressure and the like of a user, which may be acquired by testing a pulse wave of the user or testing other biological characteristic signals of the user. In other words, the biological information detection system 170 in the embodiment of the present application may be configured to detect the pulse wave of the user and obtain one or more biological characteristic information of the user base don calculation and analysis of the pulse wave.

In some embodiments, the electronic device 100 may omit at least one part of the above parts, or may further include other parts, which will not be described in detail here.

Specifically, the embodiment of the present application relates to a detection apparatus for biological characteristic information, which may be applied to the biological information detection system 170 in FIG. 1 and is arranged in the electronic device 100 in FIG. 1. More specifically, the detection apparatus for biological characteristic information in the embodiment of the present application may be configured to detect a blood pressure, and has the advantages of portability, noninvasive measurement, high measurement accuracy and the like.

For the convenience of understanding, related concepts which the present application relates to are described first.
(1) Pulse Wave.

The pulse wave refers to the periodic fluctuation of arterial wall caused by periodic change of pressure and volume in artery during periodic contraction and relaxation of heart, that is, the periodic beating of the heart pushes blood to run along blood vessels to generate pulse wave. Therefore, the pulse wave is affected not only by the functional state of the heart, but also by vascular resistance, vascular elasticity and blood viscosity in all levels of arteries. Changes in the physiological characteristics of the cardiovascular system will cause changes in the intensity, shape, rhythm and rate of pulse wave signals. Therefore, physiological and pathological information included in the pulse wave signal may be extracted by analyzing and researching the characteristics of the pulse wave signal so as to provide help for early diagnosis and prevention of diseases related to the cardiovascular system.

Photo plethysmography pulse wave is generally obtained by a photoelectric sensor through detection, which is usually detected by a photo plethysmography (PPG) method. A curve of a blood volume changing with time is obtained by the PPG method, that is, a photo plethysmographic pulse wave waveform diagram. The photo plethysmography pulse wave is also written as a photo plethysmography signal or a PPG signal.

Figure 2:
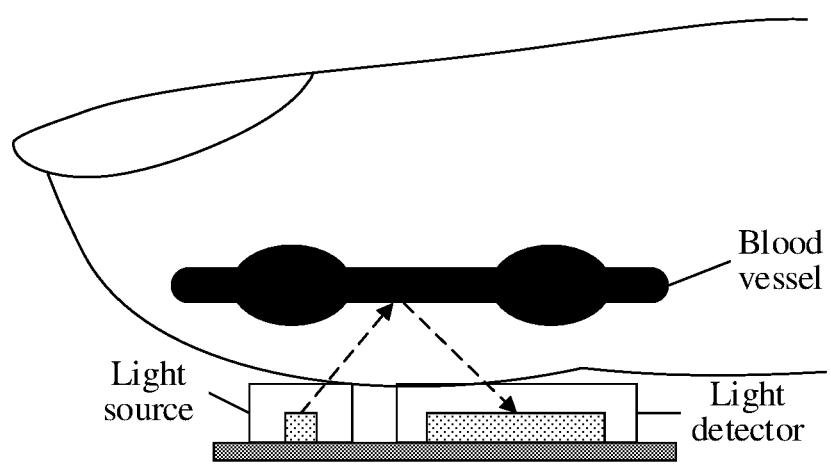
FIG. 2 is a structural schematic diagram of a device for obtaining photo plethysmography by a photoelectric sensor.

Specifically, FIG. 2 is a structural schematic diagram of a device for obtaining photo plethysmography by a photoelectric sensor.

As shown in FIG. 2, when a light source emits a light beam with a certain wavelength to irradiate the surface of human skin (for example, finger skin shown in FIG. 2), the contraction and expansion of the blood vessel will affect the transmission of light (for example, light passing through fingertips during PPG transmission) or the reflection of light (for example, light from near the surface of fingers during PPG reflection) during each heartbeat. When the light passes through the skin tissue and then is reflected to a light detector, the light will be attenuated to a certain extent. The absorption of light by muscles, bones, veins and other connecting tissues is basically unchanged (if there is no substantial movement at the measurement part), but arteries will be different. Because there is blood pulsation in the arteries, the absorption of light will naturally change. Therefore, after the light detector converts optical signals reflected and/or transmitted by the human body into electric signals, since the absorption of the optical signals by the artery changes and the absorption of the optical signals by other tissues is basically unchanged, the obtained signals may be divided into a direct current (DC) signal and an alternating current (AC) signal, and the blood flowing characteristic can be reflected by extracting the AC signal from the obtained signals.

Figure 3:
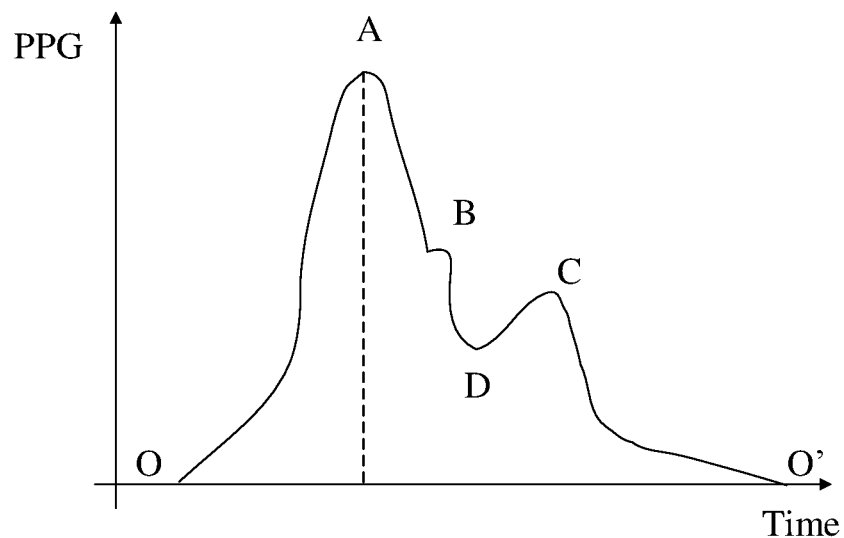
FIG. 3 is a waveform characteristic diagram of photo plethysmography.

FIG. 3 shows a waveform characteristic diagram of photo plethysmography pulse wave.

As shown in FIG. 3, a complete pulse waveform has four important characteristic points A, B, C and d, including ascending and descending branches. As shown in FIG. 3, A is called a main wave, B is called a tidal wave, C is called a dicrotic wave crest, D is called a dicrotic wave trough, OA is an ascending branch of the main wave, and OO' is a pulse wave period.

The OA segment is the ascending branch of the pulse waveform, which is due to that the left ventricle contracts and ejects blood and arterial blood pressure increases rapidly to form the expansion of the arterial wall. The point O is the starting point of a cardiac ejection period, and the point A is the highest point of arterial pressure, reflecting the maximum of the pressure and volume in the artery.

The AD segment is the front segment of the descending branch of the pulse waveform, which is formed by the process that the blood ejection speed begins to decrease at the later stage of ventricular ejection, resulting in that the volume of blood flowing from aorta to the surrounding is greater than the volume of the blood flowing into the aorta, the artery changes from expansion to contraction, and the arterial blood pressure gradually decreases. The point B is the stop point of left ventricular ejection and the peak point of reflected wave, which is also called the peak of tidal wave and reflects the tension, compliance and peripheral resistance of the artery blood vessel. The point D is the valley point of the tidal wave, that is, a demarcation point between contraction and relaxation of the heart.

The DO' segment is the rear segment of the descending branch of the pulse waveform, also called dicrotic wave, which is formed by ventricular relaxation of ventricle relaxes, continuous decrease of the arterial blood pressure and backflow of blood in the aorta towards the ventricular direction. The functional status of the aorta, the blood vessel elasticity and the flowing status of blood are reflected.
(2) Blood Pressure Detection Based on Pulse Wave.

In an existing technical theory, pulse wave velocity (PWV) and pulse wave transit time (PTT) have a linear relation with the blood pressure, and blood pressure parameters may be calculated according to PWV or PTT and the related data models.

Specifically, PTT refers to the transit time of the pulse wave from the heart to the measurement part during arterial ejection; and PWV may be calculated through PTT and the position relation between the measurement part and the heart.

At present, since the pulse wave velocity (PWV) is difficult to measure, an existing PWV-based blood pressure detection method depends on PTT detection.

In some methods, the PTT may be detected through an electrocardiography (ECG) and PPG combined blood pressure detection technology, so that the blood pressure parameter is obtained through estimation.

Figure 4:
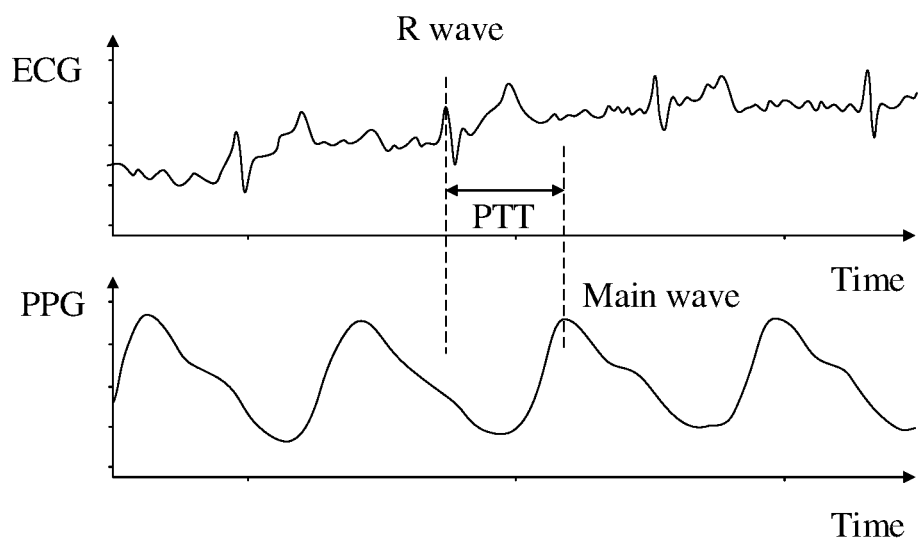
FIG. 4 is a schematic diagram of a relative relation among an ECG waveform, a PPG waveform and PTT.

FIG. 4 shows a relative relation among an ECG waveform, a PPG waveform and PTT.

As shown in FIG. 4, in the ECG waveform, R wave represents ventricular contraction, and a time interval from the R wave in the ECG waveform to the main wave in the PPG waveform may be represented as PPT. Or PPT may be represented by a time interval from the R wave in the ECG waveform to other feature points in the PPG waveform.

Specifically, a blood pressure value detected by the method according to PTT and a functional equation is a high-frequency component of a systolic blood pressure (SBP), but a low-frequency component of the systolic blood pressure needs to be measured by a more accurate blood pressure measurement method such as an auscultatory method or an oscillometric method. The finally accurate systolic blood pressure value can be determined according to the sum of the low-frequency component and the high-frequency component of the systolic blood pressure. Further, a more accurate diastolic blood pressure (DBP) value may be obtained according to a functional equation among the PTT, the more accurate SBP and the DBP. In other words, it is necessary to regularly measure an accurate blood pressure low-frequency component by the method and through an external device such as a sphygmomanometer. The blood pressure value detected according to the PPT detection method is calibrated, so that a more accurate blood pressure detection result is obtained.

In addition to the above methods for determining the blood pressure according to the PWV or PTT, the blood pressure or other biological characteristic parameters may be determined through pulse wave analysis (PWA).

Specifically, characteristic parameters in the pulse wave may be extracted, the characteristic parameter with the best correlation with the blood pressure is found by analyzing the correlation between the characteristic parameter and the blood pressure and is used as a variable for blood pressure measurement, and then regression analysis is performed to establish a regression equation for blood pressure measurement.

Optionally, an amplitude of any characteristic point in the pulse wave shown in FIG. 3 or a time difference between any two characteristic points may be used as a characteristic parameter, the correlation between the characteristic parameter and the blood pressure is analyzed through a large amount of experimental data, and a regression equation is established. In the actual blood pressure measurement process, the pulse wave is detected and the characteristic parameter is extracted from the pulse wave, so that the blood pressure value is measured according to the characteristic parameter and the regression equation.

Therefore, based on the above description, it may be seen that the pulse wave contains abundant biological characteristic information and various kinds of biological characteristic information may be extracted from the pulse wave by detecting and analyzing the pulse wave. However, in the actual detection process, due to the influence by various factors such as environment and human body differences, the detected pulse wave has great interference and poor quality, so the biological characteristic information detected by the pulse wave with poor quality has low accuracy. Furthermore, it may be seen from the above description of blood pressure detection that the blood pressure parameter obtained on the basis of PTT detection is not an absolute blood pressure parameter, and it is also necessary to further calibrate the blood pressure value measured by the sphygmomanometer to obtain a more accurate blood pressure detection result, so that the convenience of user blood pressure detection and the user experience will be affected.

Based on this, the present application provides a detection apparatus for biological characteristic information. There is no need for an additional device such as a sphygmomanometer to assist in calibration and no need for an electronic device to provide an airbag and other devices to apply a pressure to a user. Instead, the detection apparatus is actively pressed by the user, and the pulse wave signal and the pressure signal at the pressure applying part of the user on the detection apparatus are detected. The pressure signal and the pulse wave signal correspond to each other and are not two independent and unrelated signals, that is, the pulse wave signal is a corresponding pulse wave signal when the user applies the pressure signal, so that the pulse wave signal contains pulse wave change information caused by pressure change. Compared with the situation where no pressure is applied to the human body, the pulse wave signal detected by the detection apparatus in the embodiment of the present application is less interfered, and the pulse wave signal contains pulse wave change information caused by pressure change. The biological characteristic information is detected on the basis of the pulse wave signal and the pressure signal, so that the accuracy of the detection result can be improved and the detection apparatus is convenient to carry.

Figure 5:
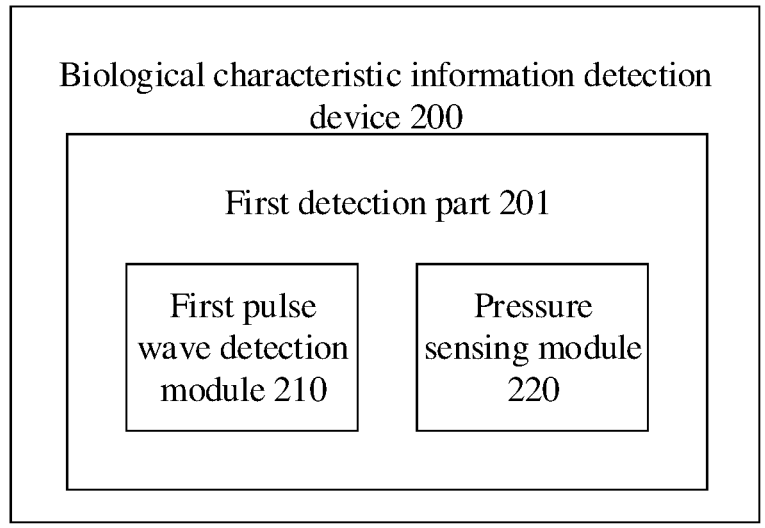
FIG. 5 is a schematic structural block diagram of a detection apparatus for biological characteristic information according to an embodiment of the present application.

FIG. 5 is schematic structural block diagram of a detection apparatus for biological characteristic information according to the present application.

As shown in FIG. 5, the detection apparatus for biological characteristic information 200 may include: a first detection part 201. The first detection part 201 may include:

a first pulse wave detection module 210, configured to detect a first pulse wave signal of a user when the user presses the first pulse wave detection module 210; and a pressure sensing module 220, configured to detect a pressure signal when the user presses the first pulse wave detection module 210, where the pressure signal corresponds to the first pulse wave signal, and the pressure signal and the first pulse wave signal are used to detect first biological characteristic information of the user.

Optionally, in the embodiment of the present application, the pressure sensing module 220 includes a pressure sensor, for sensing a pressure signal applied to the pressure sensor. For example, the user presses the first pulse wave detection module 210 while pressing the pressure sensing module 220, then the pressure sensor in the pressure sensing module 220 is configured to directly detect a pressing pressure of the user. Or when the user presses the first pulse wave detection module 210, the first pulse wave detection module 210 presses the pressure sensing module 220, then the pressure sensor in the pressure sensing module 220 is configured to detect a pressing pressure on the pressure sensing module 220 by the first pulse wave detection module 210 so as to detect the pressing pressure of the user. Or when the user presses the first pulse wave detection module 210, the pressure sensing module 220 may detect the pressing pressure of the user by other methods, which is not specifically limited by the embodiment of the present application.

The pressure sensor includes, but is not limited to: a piezoelectric pressure sensor, a piezoresistive pressure sensor, a capacitive pressure sensor an inductive pressure sensor or other types of pressure sensors, which is not specifically limited by the embodiment of the present application.

As an example, the pressure sensor in the pressure sensing module 220 is a piezoresistive pressure sensor. Specifically, the piezoresistive pressure sensor mainly detects a pressure signal based on piezoresistive effect. The piezoresistive effect is used to describe resistance change of a material under a mechanical stress, that is, the piezoresistive pressure sensor is configured to detect resistance change of the material to detect a pressure signal acting on the material.

Optionally, in the embodiment of the present application, the first pulse wave signal detected by the first pulse wave detection module 210 may be a photo plethysmography (PPG) signal. The method for measuring the PPG signal is easy to implement, so the following takes the case where the PPG signal detected by the first pulse wave detection module 210 serves as the first pulse wave signal as an example for illustration.

Figure 6:
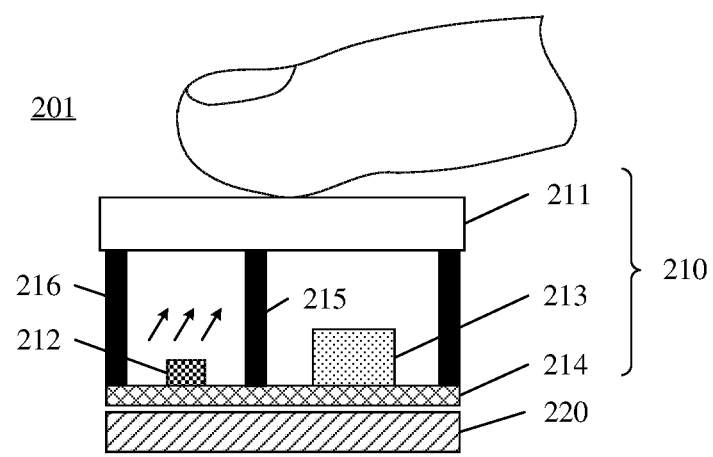
FIG. 6 is a structural schematic diagram of a first detection part according to an embodiment of the present application.

As an example, FIG. 6 shows a structural schematic diagram of the above first detection part 201.

As shown in FIG. 6, if the first pulse wave detection module 210 is a PPG detection module, the first pulse wave detection module 210 may include: a cover 211, a first light source 212 and a first light detection 213.

Specifically, the cover 211 is a light-transmitting cover prepared by a transparent material, where the transparent material may be a material with high light transmittance such as glass or resin so as to reduce the attenuation of an optical signal when passing through the cover.

When the user's finger presses the cover 211, the first light source 212 is configured to transmit an optical signal to the user's finger, the optical signal is received by the first light detector 213 after being reflected or scattered by blood vessels in the finger, and then a PPG signal is formed after photoelectric conversion and electrical signal processing.

In addition, in the above process, the user's finger presses the cover 211 and the pressing pressure of the user's finger is generally unstable. In other words, the pressing pressure of the user's finger is generally variable. Therefore, under the changing pressing pressure, the blood vessels in the finger are squeezed to different degrees, and the blood volume, the blood pressure and other related parameters are changing accordingly, so the PPG signal formed by the first light detector 213 is changing with the pressing pressure, and the biological characteristic information of the user, such as blood pressure parameter of the user, is determined according to the changing degree of the PPG signal under different pressing pressures. Compared with determining the blood pressure parameter of the user directly according to a PPG signal, the above solution can improve the accuracy of blood pressure detection or the accuracy of other biological characteristic parameters.

Optionally, in some implementation manners, the pressure sensing module 220 and the above first pulse wave detection module 210 are arranged side by side and may be located on the same plane.

Preferably, in some other implementation manners, the pressure sensing module 220 and the above first pulse wave detection module 210 are stacked.

As an example, as shown in FIG. 6, the first pulse wave detection module 210 and the pressure sensing module 220 are stacked up and down. When the user's finger presses the cover 211, that is, when the user's finger presses the first pulse wave detection module 210, the first pulse wave detection module 210 is configured to detect the PPG signal of the user's finger. Meanwhile, the pressure sensing module 220 may be configured to synchronously detect the pressing pressure of the user's finger. At this time, the pressure signal detected by the pressure sensing module 220 and the PPG signal detected by the first pulse wave detection module 210 are the pressure signal and the PPG signal of the same part of the user's finger. If the pressure sensing module 220 and the first pulse wave detection module 210 are arranged side by side, the pressure signal detected by the pressure sensing module 220 and the PPG signal detected by the first pulse wave detection module 210 are not the pressure signal and the PPG signal of the same part of the user's finger. Therefore, by adopting the technical solution of the embodiment of the present application, the first pulse wave detection module 210 and the pressure sensing module 220 are stacked, the pressure signal and the PPG signal have better correspondence, and the biological characteristic information detected by the pressure signal and the PPG signal has higher accuracy.

Therefore, it may be seen from the above description that the first pulse wave detection module and the pressure sensing module are stacked together; the pressure signal is detected while the first pulse wave signal is detected, and the pressure signal and the first pulse wave signal are synthesized together for detecting biological characteristic parameters such as blood pressure, blood oxygen and heart rate, so that the accuracy of detecting biological characteristic parameters may be improved, thereby improving the use experience of the user.

Continuously referring to FIG. 6, it shows a structural schematic diagram of the first detection part 201. As shown in FIG. 6, the first pulse wave detection module 210 may further include a substrate 214, where the above first light source 212 and the first light detector 213 are arranged on the substrate 214. Optionally, the substrate 214 includes, but is not limited to a printed circuit board (PCB) or other types of circuit boards, for being electrically connected to the first light source 212 and the first light detector 213. Specifically, the substrate 214 may further be connected to a processor or a controller of an electronic device through other electrical connection devices; and a control signal generated by the processor or the controller may be transmitted to the first light source 212 and the first light detector 213 through the substrate 214 for controlling a working time sequence of the first light source 212 and the first light detector 213. In addition, an electrical signal generated after the first light detector 213 receives the optical signal is also transmitted to the processor or the controller of the electronic device through the substrate 214 to perform data processing, and forming a PPG signal and detecting biological characteristic information.

Further, as shown in FIG. 6, in the first pulse wave detection module 210, a spacer 215 is provided to arrange between the first light source 212 and the first light detector 213. The spacer 215 is configured to prevent an optical signal emitted by the first light source 212 from directly arriving at the first light detector 213 and forming an interference light signal for biological characteristic information detection. In the optical signal received by the first light detector 213, if the optical signal reflected or transmitted by the finger is stronger and an ambient light signal or a light source light signal and other interference light signal is weaker, the quality of the PPG signal detected by the first light detector 213 is higher, and the accuracy of detecting biological characteristic information is higher.

As an example, in the embodiment shown in FIG. 6, the first pulse wave detection module 210 may further include a bracket 216. Specifically, the bracket 216 is arranged on a peripheral edge of the substrate 214 and is configured to support the cover 211 to be arranged above the first light source 212 and the first light detector 213. Further, the above spacer 215 is also located between the cover 211 and the substrate 214 and may be configured to further support the cover 211 so as to improve the mechanical stability of the apparatus.

Optionally, a combination of the bracket 216, the cover 211 and the substrate 214 may form a closed chamber. Further, the spacer 215 is configured to divide the closed chamber into two parts. The first light source 212 and the first light detector 213 are located into the two chambers respectively. The two chambers can protect the first light source 212 and the first light detector 213 well and can avoid interference formed by light other than the first light source, so that the accuracy of the PPG signal can be improved.

Optionally, the two chambers may be filled with air, then the transmission of the optical signal is less affected. Or the above two chambers may also be filled with a transparent medium layer with high light transmittance, then the overall stability of the apparatus can be improved.

In the embodiment shown in the above FIG. 6, the first pulse wave detection module 210 includes single first light source 212 and single first light detector 213. In this embodiment, the first pulse wave detection module 210 has a simple structure and is beneficial to realize the miniaturization of the apparatus and reduce the cost of the apparatus on the basis of detecting the PPG signal.

Optionally, the first light source 212 includes, but is not limited to a point light source, for example, a light-emitting diode (LED), a laser diode (LD) or an infrared emitting diode; and the first light source 212 may also be a linear light source or a planar light source, which is not specifically limited by the embodiment of the present application. The first light source 212 may be configured to emit an optical signal of one or more target wavebands. As an example, the target waveband may be a red light waveband or a green light waveband.

Optionally, the first light detector 213 includes, but is not limited to, a photodiode (PD), a phototriode and the like, and is configured to perform photoelectric conversion and convert the received optical signal reflected or transmitted by the finger into a corresponding electrical signal. Optionally, the first light detector 213 may further include an optical component and a processing circuit. As an example, the optical component may be arranged above the PD and is configured to guide more effective optical signals to enter the PD so as to improve the optical detection efficiency of the PD. The processing circuit may be configured to process the electrical signal acquired through PD processing, which is beneficial for the subsequent processor to process the electrical signal to acquire a PPG signal with higher quality. Or the processing circuit may also be configured to process the electrical signal acquired through PD processing to acquire a PPG signal and then transmit the PPG signal to the processor for detecting biological characteristic information.

Figure 7:
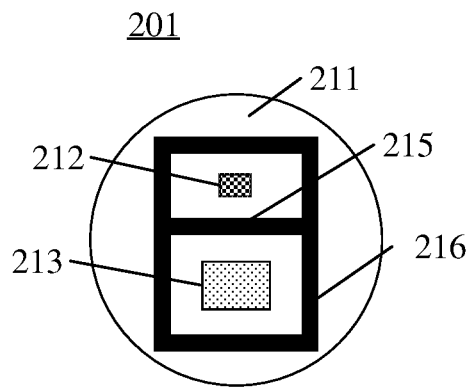
FIG. 7 is a schematic top view of the first detection part in FIG. 6.

FIG. 7 shows a top view of the first detection part 201 in FIG. 6.

As shown in FIG. 7, the cover 211 in the first pulse wave detection module 210 may be of a circle, a waist circle or other regular or irregular shapes. The first light source 212 and the first light detector 213 are located below a middle area of the cover 211, so that the optical signal can be transmitted to a good contact area of the finger on the cover 211, and the optical signal reflected or transmitted by the finger at the contact area is detected.

As an example, as shown in FIG. 7, a section of the bracket 216 is frame-shaped, and a local area or all of the area at the periphery of the bracket 216 may be further provided with a supporting structure for supporting the cover 211. Or in other implementation manners, the bracket 216 has a cylindrical structure and is internally provided with a cavity for accommodating the first light source 212 and the first light detector 213; and a section shape of the bracket 216 is the same as or similar to that of the cover 211.

Optionally, there may be a plurality of first light sources 212 in the first pulse wave detection module 210, and there may also be a plurality of first light detectors 213 in the first pulse wave detection module 210.

For example, FIG. 8 to FIG. 11 show various other top views of the first detection part 201.

Figure 8:
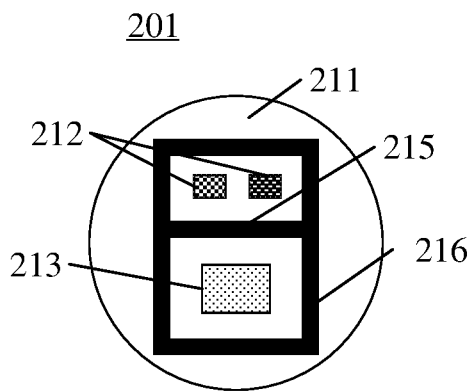
FIG. 8 to FIG. 11 are several other schematic top views of a first detection part according to an embodiment of the present application.
Figure 9:
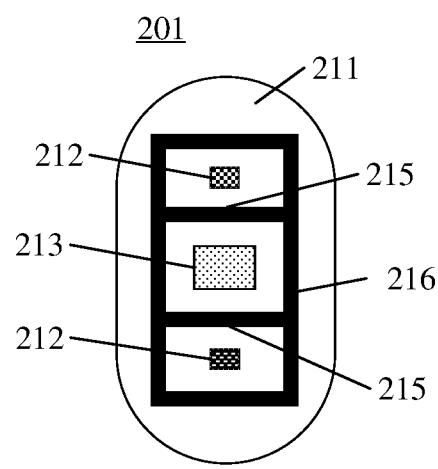

As shown in FIG. 8 and FIG. 9, the first pulse wave detection module 210 includes two first light sources 212 and one first light detector 213. Specifically, the two first light sources 212 are configured to emit optical signals of different target wavebands respectively. As an example, the two first light sources 212 emit an optical signal of a red light waveband and an optical signal of a green light waveband respectively. Further, the two first light sources 212 are configured to emit optical signals at different time respectively; and one first light detector 213 receives a red light signal passing through a finger at a first moment and receives a green light signal passing through the finger at a second moment.

As a possible implementation manner, in FIG. 8, one spacer 215 divides a closed chamber formed by the bracket 216, the cover 211 and the substrate 214 into two chambers, where two first light sources 212 are located in the same chamber, and a first light detector 213 is located in the other chamber. As another possible implementation manner, in FIG. 9, two spacers 215 divide a closed chamber formed by the bracket 216, the cover 211 and the substrate 214 into three chambers, where the first light detector 213 is located in the middle chamber, and two first light sources 212 are located in the chambers on two sides respectively.

By the solution of the embodiment, a plurality of PPG signals of different wavebands are acquired, and biological characteristic parameters such as blood oxygen and heart rate can be detected according to the plurality of PPG signals of different wavebands, and the accuracy of detecting the biological characteristic parameters can be improved; in addition, the biological characteristic information is detected through the plurality of PPG signals of different wavebands and the pressure signal, so that the accuracy of detecting the biological characteristic information can also be improved.

Figure 10:
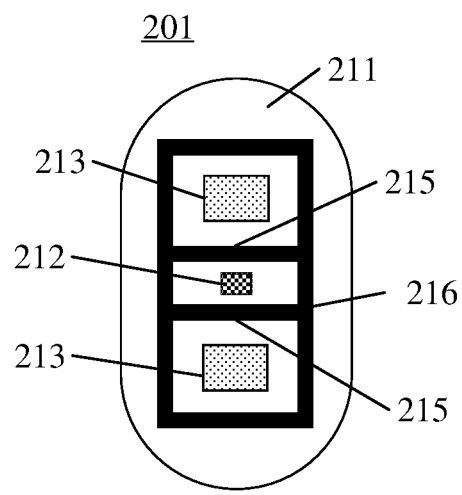

As shown in FIG. 10, the first pulse wave detection module 210 includes one first light source 212 and two first light detectors 213. Similar to the above FIG. 9, one first light source 212 is located in the middle chamber, and the two first light detectors 213 are located in the chambers on two sides respectively.

By the solution of this embodiment, a plurality of photoelectric sensors are provided, so that more optical signals passing through a finger can be received. A plurality of optical signals received by the plurality of photoelectric sensors and passing through the finger are used to process and form a plurality of PPG signals. The plurality of PPG signals are used to comprehensively detect biological characteristic parameters, so that the accuracy of detecting the biological characteristic parameters can also be improved.

Figure 11:
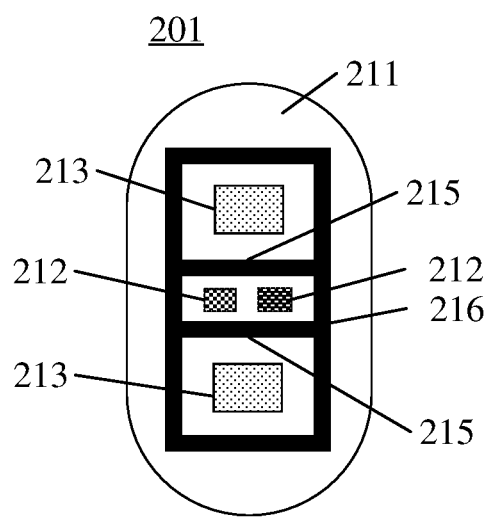

As shown in FIG. 11, the first pulse wave detection module 210 includes two first light sources 212 and two first light detectors 213, where the two first light source 212 are located in the middle chamber, and the two first light detectors 213 are located in the chambers on two sides respectively.

By the technical solution of this embodiment, the advantages of the first pulse wave detection module 210 in the above FIG. 8 to FIG. 10 may be synthesized, which will not be elaborated in detail here.

Optionally, the first detection part 201 in any of the above implementation manners may be arranged in any surface of an electronic device, which is convenient for user to press with finger. As an example, the first detection part 201 may be arranged on a side or a back of the electronic device.

Specifically, if the first detection part 201 is arranged on the side of the electronic device, additional space on the front side or back of the electronic device can be prevented from being occupied, and the aesthetic degree of the electronic device can be increased. Furthermore, if the electronic device is a wearable device, for example, a smartwatch and the like, the first detection part 201 is arranged on a side of the smartwatch, which does not affect the wearing experience on the back of the watch and affect the screen display on the front side of the watch, makes the appearance of the watch more fashionable and beautiful and is convenient for the finger to press the first detection part 201, so that the user experience can be improved.

Optionally, the above first detection part 201 may be fixedly arranged on a surface of the electronic device.

Preferably, the above first detection part 201 may be arranged at a first button of the electronic device. Specifically, a cavity is formed in a shell of the first button. The first pulse wave detection module 210 is at least partially arranged in the cavity of the first button. The pressure sensing module 220 is at least partially arranged in the cavity of the first button. Compared with the technical solution that the first detection part 201 is fixedly arranged on the surface of the electronic device, by adopting the solution of the embodiment of the present application, the first pulse wave detection module 210 and the pressure sensing module 220 may at least partially reuse the space of the cavity in the first button, thereby facilitating the miniaturization of the electronic device. In addition, the user may rapidly find the first button where the first pulse wave detection module 210 and the pressure sensing module 220 are located, and can perform pressing operation on the first button conveniently, so that the use experience of the user is improved.

In some examples, the above first button may be a button of the electronic device for performing other functions, for example, a sound button or a power button. In other words, a function button of the electronic device is reused as the first button. After integrating the first pulse wave detection module 210 and the pressure sensing module 220, the first button is also configured to perform a biological characteristic information detection function in addition to a sound function or a power function. By this implementation manner, a plurality of functions of the electronic device are integrated into the same button, which facilitates the miniaturization development and design of the electronic device, is favorable for the production and manufacturing of the electronic device, reduces the manufacturing process and the manufacturing cost, and is also favorable for improving the appearance of the electronic device.

In some other examples, the above first button may also be a button specially configured to perform a biological characteristic information detection function in the electronic device. By this implementation manner, only the first pulse wave detection module 210 and the pressure sensing module 220 are arranged in the first button, so that maintenance and change of the first pulse wave detection module 210 and the pressure sensing module 220 are facilitated, and the stability of biological characteristic information detection is improved.

Figure 12:
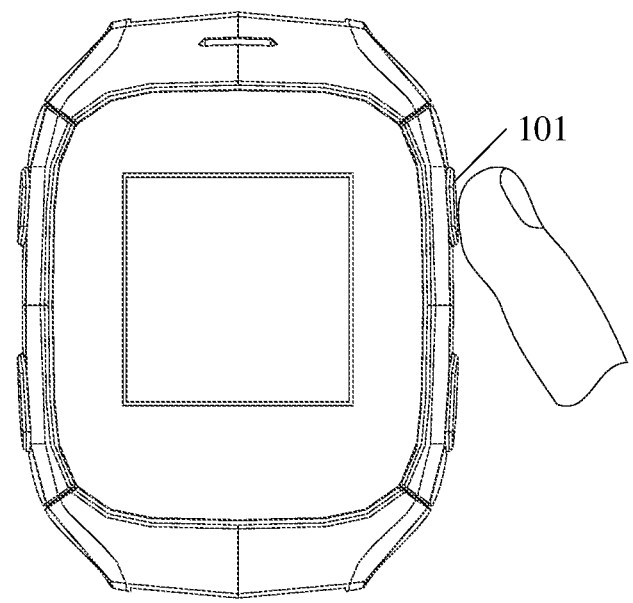
FIG. 12 is a schematic top view of an electronic device according to an embodiment of the present application.
Figure 13:
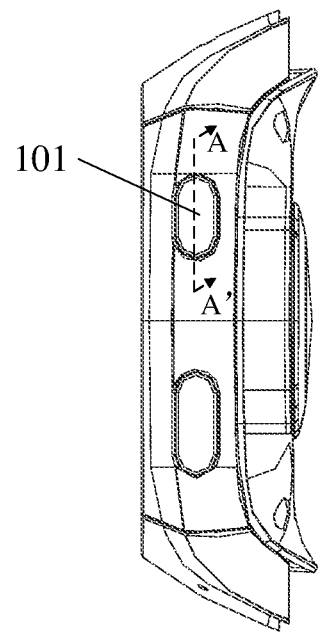
FIG. 13 is a schematic side view of the electronic device shown in FIG. 12.

FIG. 12 and FIG. 13 show a top view and a side view of an electronic device, that is, a front side and a side of the electronic device.

As an example, the electronic device shown in FIG. 12 and FIG. 13 is a smartwatch. A first button 101 is arranged on a side of the smartwatch, and the first pulse wave detection module 210 and the pressure sensing module 220 may be at least partially arranged in the first button 101.

In a general application scene, the smartwatch is worn on the wrist of the user's left hand, and the first button 101 provided by the embodiment of the present application may be arranged on a button on a right side surface of the watch, which is convenient for the user to press.

Figure 14:
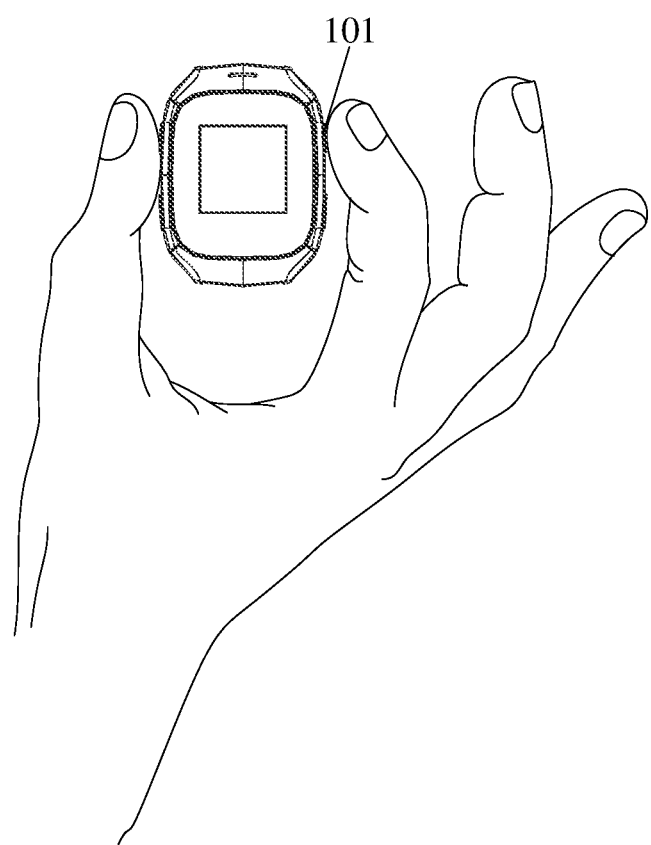
FIG. 14 is a schematic diagram of a user pressing mode according to an embodiment of the present application.

Further, in the embodiment of the present application, in order to improve the pressing stability of the user's finger, the user may be prompted by a display screen of the electronic device or other prompt modes to press the first button 101 by the pressing mode shown in FIG. 14.

As shown in FIG. 14, the user's thumb presses one side of the smartwatch, the index finger presses the other side of the smartwatch, and the thumb and the index finger press together to press the sides of the smartwatch. Optionally, the first button 101 provided by the embodiment of the present application is arranged on one side of the user's index finger and is configured to detect the pressure signal pressed by the user's index finger and the PPG signal. By adopting the embodiment of the present application, the stability of the detected pressure signal can be improved, and the PPG signal with excellent quality can be acquired, so that the accuracy of detecting the biological characteristic information can be improved.

Further, as shown in FIG. 14, other sensing modules may be arranged on a side where the user's thumb is located for detecting vital signs of the user and providing various functions of the watch. For example, a temperature sensing module, a light sensing module, a biological impedance sensing module, an ECG sensing module and the like may be provided, which are not specifically limited by the embodiment of the present application.

Figure 15:
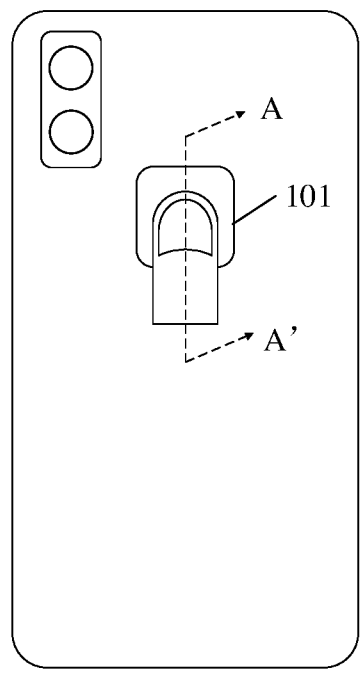
FIG. 15 is a schematic rear view of an electronic device according to an embodiment of the present application.

FIG. 15 shows a rear view of another electronic device, that is, a back of the electronic device.

As an example, the electronic device shown in FIG. 15 is a mobile phone. A first button 101 is arranged on a backside of the watch, and the first pulse wave detection module 210 and the pressure sensing module 220 may be at least partially arranged in the first button 101.

When the user holds the mobile phone, the finger may press the first button 101 on the back of the mobile phone conveniently, so that the first pulse wave detection module 210 and the pressure sensing module 220 in the first button 101 may detect the pressure signal pressed by the finger and the PPG signal.

Optionally, the first button 101 in the embodiment of the present application may also be arranged on a front side or a side of a smartphone, which is not specifically limited by the embodiment of the present application.

In addition, the smartphone of the embodiment of the present application may further be provided with an ECG sensing module and other sensing modules for detecting biological characteristics, and is configured to detect vital signals of the user and provide various functions, so that the use experience of the user may be improved.

Figure 16:
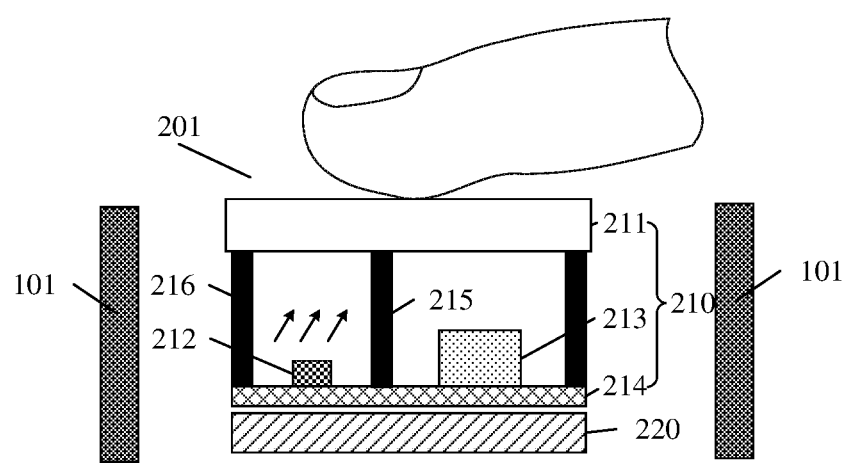
FIG. 16 is a schematic sectional view of a first button of the electronic device in FIG. 13 and FIG. 15 in an A-A' direction.

Optionally, FIG. 16 is a schematic sectional view of the first button 101 in FIG. 13 and FIG. 15 in an A-A' direction.

As shown in FIG. 16, the first button 101 includes a cavity. Optionally, the cavity may accommodate the first detection part 201 shown in FIG. 6.

The first detection part 201 includes:
- a first pulse wave detection module 210, at least partially arranged in the cavity of the first button 101 and configured to detect a first pulse wave signal of a user when the user presses the first button 101; and
- a pressure sensing module 220, at least partially arranged in the cavity of the first button 101 and configured to detect a pressure signal applied to the first button 101 by the user, where the first pulse wave signal is a corresponding pulse wave signal when the user applies the pressure signal, and the pressure signal and the first pulse wave signal are used to detect first biological characteristic information of the user.

In some implementation manners, as shown in FIG. 16, the pressure sensing module 220 and the first pulse wave detection module 210 are stacked, and the pressure sensing module 220 is located on one side, facing towards the inside of the electronic device, of the first pulse wave detection module 210.

In some other implementation manners, the pressure sensing module 220 and the first pulse wave detection module 210 may be arranged in parallel and are located on the same plane.

Optionally, as an example, the first button 101 has an independent shell, a cavity is formed in the shell, and at least part of the pressure sensing module 220 and at least part of the first pulse wave detection module 210 are arranged in the cavity.

Optionally, as another example, part of components in the first pulse wave detection module 210 and the pressure sensing module 220 may be reused as part of the shell of the first button 101, in other words, part of the shell of the first button 101 may be reused as part of the components in the first pulse wave detection module 210 and the pressure sensing module 220.

Figure 17:
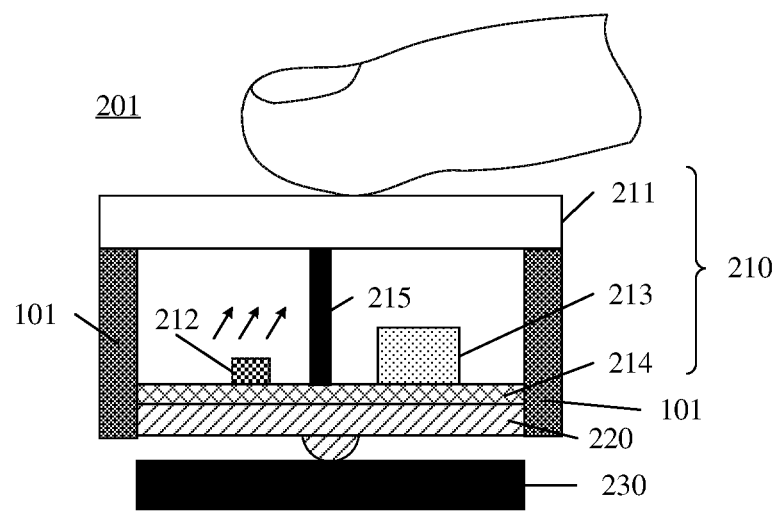
FIG. 17 is another schematic diagram of a first detection part according to an embodiment of the present application.

FIG. 17 shows a structural schematic diagram of another first detection part 201.

As shown in FIG. 17, the first pulse wave detection module 210 is fixedly connected to the shell of the first button 101, and the pressure sensing module 220 is fixedly connected to the first pulse wave detection module 210. The first detection part 201 further includes: a first structural component 230 arranged on one side of the pressure sensing module 220, and the first structural component 230 and the pressure sensing module 220 are both located on the same side of the first pulse wave detection module 210. Specifically, in the embodiment of the present application, the first structural component 230 is arranged on one side, facing towards the inside of the electronic device, of the pressure sensing module 220.

When the user presses the first button 101, the pressure sensing module 220 and the first pulse wave detection module 210 press the first structural component 230 together in a linkage way, and the pressure sensing module 220 is configured to detect an action force between the pressure sensing module 220 and the first structural component 230 so as to detect the pressure signal applied to the first button 101 by the user.

Optional, in the embodiment of the present application, the first structural component 230 may be arranged in a fixed structural component in the electronic device.

In some implementation manner, the first structural component 230 may be arranged in the cavity in the first button 101. Or in some other implementation manners, the first structural component 230 may also be a structural component in the electronic device where the first detection part 201 is located and is arranged outside the first button 101, for example, the first structural component 230 may be a shell or a middle frame of the electronic device.

As an example, the pressure sensing module 220 includes a silicon pressure sensor. The silicon pressure sensor is configured to press the first structural component 230 together with the first pulse wave detection module 210 in a linkage way. Resistance of the silicon pressure sensor changes with the change of the pressing pressure. The silicon pressure sensor has high measurement precision and stability and can obtain the measurement result of the high-precision pressure signal, so that the accuracy of detecting the biological characteristic information can be improved.

Optionally, as shown in FIG. 17, part of the shell of the first button 101 is reused as the cover 211 in the first pulse wave detection module 210, that is, the cover 211, as an interface for interacting with the user in the first button 101, is configured to receive the pressing of the user. When the user presses the first button 101, the cover 211 is pressed. Other components of the first pulse wave detection module 210 may be connected to the shell of the first button 101 by connecting to the cover plate 211.

Further, in the embodiment shown in FIG. 17, part of the shell of the first button 101 may also be reused as the bracket 216 in the first pulse wave detection module 210. Or in other implementation manners, other part of the shell of the first button 101 may also be reused as the substrate 214 in the first pulse wave detection module 210.

Compared with the situation where the first button 101 has the independent shell and is not reused as part of components in the first pulse wave detection module 210, the implementation manner shown in FIG. 17 may further reduce the manufacturing cost of the first button 101 and the first pulse wave detection module 210, thereby reducing the manufacturing cost of the electronic device.

Figure 18:
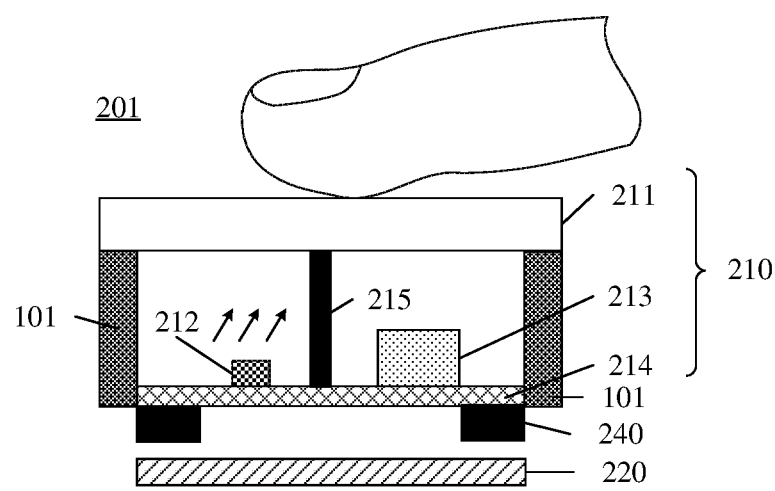
FIG. 18 is another schematic diagram of a first detection part according to an embodiment of the present application.

FIG. 18 shows a structural schematic diagram of another first detection part 201.

As shown in FIG. 18, the first pulse wave detection module 210 is fixedly connected to the shell of the first button 101, and the pressure sensing module 220 is separably arranged on one side of the first pulse wave detection module 210. The first detection part 201 further includes: a second structural component 240, fixedly connected to the first pulse wave detection module 210. The second structural component 240 and the pressure sensing module 220 are arranged on the same side of the first pulse wave detection module 210. Specifically, in the embodiment of the present application, the second structural component 240 is arranged on one side, facing towards the inside of the electronic device, of the first pulse wave detection module 210.

When the user presses the first button 101, the second structural component 240 and the first pulse wave detection module 210 press the pressure sensing module 220 together in a linkage way. The pressure sensing module 220 is configured to detect an action force between the pressure sensing module 220 and the second structural component 240 so as to detect the pressure signal pressed by the user.

Optionally, in some implementation manners, the pressure sensing module 220 includes a strain sensor. The strain sensor includes: a strain gauge and an elastic component, where the strain gauge may be a resistance strain gauge and is arranged on a surface of the elastic component, and the strain change of the elastic component is converted into resistance change, so that the force of the stain caused by the elastic component is detected.

In the embodiment of the present application, the user presses the first pulse wave detection module 210, the first pulse detection module 210 and the second structural component 240 apply a pressure to the elastic component, and the strain gauge is configured to detect the pressure applied to the elastic component so as to detect the pressure signal pressed by the user. The pressure signal detected by the implementation manner also has high precision and is beneficial to improve the accuracy of detecting the biological characteristic information.

Figure 19:
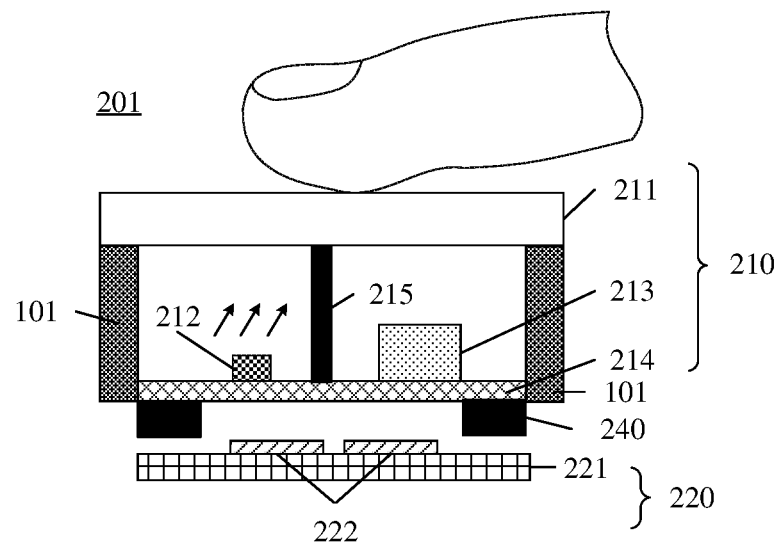
FIG. 19 is another schematic diagram of a first detection part according to an embodiment of the present application.

As an example, FIG. 19 shows a structural schematic diagram of another first detection part 201.

As shown in FIG. 19, the pressure sensing module 220 includes an elastic component 221 and a strain gauge 222, where the elastic component 221 may be of a sheet structure and may be specifically a metal sheet. The strain gauge 222 may be arranged in a middle area of a surface of the elastic component 221, the second structural component 240 is configured to press an edge area on the surface of the elastic component 221 so as to deform the elastic component 221, and the strain gauge 222 is configured to detect the deformation so as to detect the pressure signal pressed by the user.

It may be understood that in addition to the structure shown in FIG. 19, the strain sensor in the pressure sensing module 220 may also be of a structure on other related arts, which is not specifically limited by the embodiment of the present application.

It may also be understood that in addition to the piezoresistive pressure sensor, the pressure sensing module 220 shown in FIG. 17 to FIG. 19 may further include other types of pressure sensors. For other types of pressure sensors, a corresponding pressure detection structure may be designed in the pressure sensing module 220. The design of other types of pressure sensors and the corresponding pressure detection structure is not discussed in detail here.

Optionally, as shown in FIG. 18 and FIG. 19, part of the shell of the first button 101 is reused as the cover 211 in the first pulse wave detection module 210, that is, the cover 211, as an interface for interacting with the user in the first button 101, is configured to receive the pressing of the user. When the user presses the first button 101, the cover 211 is pressed. Other components of the first pulse wave detection module 210 may be connected to the shell of the first button 101 by connecting to the cover plate 211.

Further, in the embodiment shown in FIG. 18 and FIG. 19, part of the shell of the first button 101 may also be reused as the bracket 216 in the first pulse wave detection module 210. Or in other implementation manners, other part of the shell of the first button 101 may also be reused as the substrate 214 in the first pulse wave detection module 210.

In the first detection part 201 shown in FIG. 17 above, if the first structural component 230 is a fixed structural component and when the user presses strongly, the action between the first structural component 230 and the pressure sensing module 220 is large, which is liable to damage the pressure sensing module 220.

Based on this problem, in the embodiment of the present application, an elastic module is added to provide a movable distance for the pressure sensing module 220 and the first structural component 230 and limit the movable distance within a preset range so as to limit the action force between the pressure sensing module 220 and the first structural component 230 within in the preset range and avoid damage to the pressure sensing module 220 caused by excessive action force.

Figure 20:
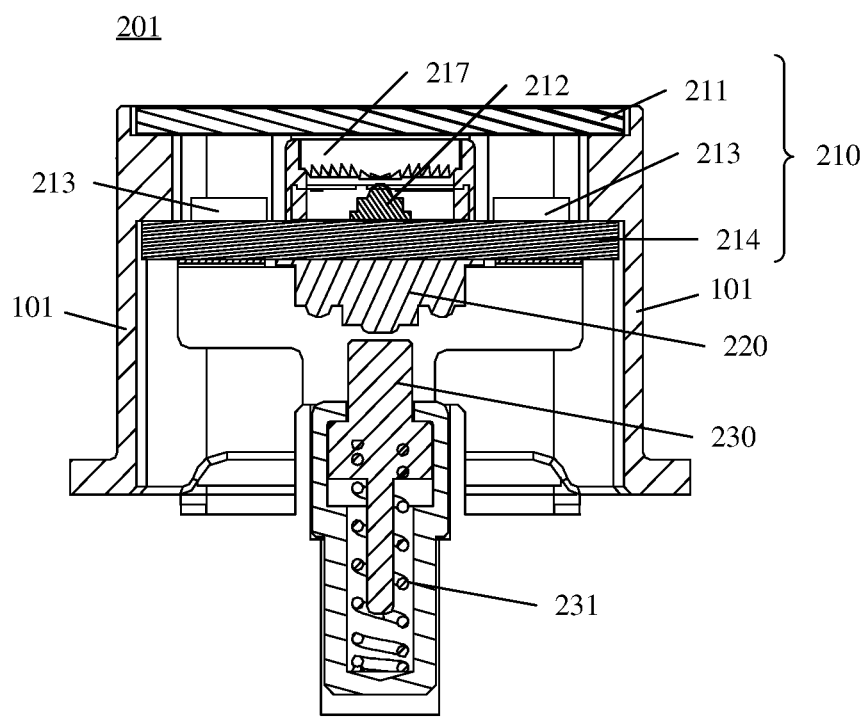
FIG. 20 is another schematic diagram of a first detection part according to an embodiment of the present application.

FIG. 20 shows a structural schematic diagram of another first detection part 201, which may be relatively specific implementation manner of the first detection part 201 shown in FIG. 17.

As shown in FIG. 20, the first detection part 201 further includes an elastic module 231. Specifically, the elastic module 231 is connected to the above first structural component 230 and is arranged on a lower part of the first structural component 230, that is, arranged on one side, facing towards the inside of the electronic device, of the first structural component 230; furthermore, the elastic module is also connected to the shell, so that the elastic module may deform along with the first structural component and may also limit the travel of the first structural component.

Optionally, in the embodiment shown in FIG. 20, part of the shell of the first button 101 is reused as the cover 211. When the user presses the first button 101, that is, the user presses the cover 211, the first pulse wave detection module 210, the pressure sensing module 220 and the first structural component 230 are deformed downwards together in a linkage way and compress the elastic module 231, and the elastic module 231 generates a corresponding elastic force acting on the first structural component 230. Further, the first structural component 230 generates an action force corresponding to the elastic force on the pressure sensing module 220, and the pressure sensing module 220 is configured to detect the action force so as to detect the pressing pressure of the finger.

With the increase of the pressing pressure of the user, the elastic module 231 is gradually compressed until the maximum compression amount is reached. At this time, the position of the first structural component 230 is fixed, and if the user feels that he cannot continue to press down, the user will stop increasing the pressing force, so that damage to the pressure sensing module 220 caused by excessive pressing pressure of the finger can be avoided.

In the embodiment of the present application, the maximum compression amount of the elastic module 231 limits the movable distance of the pressure sensing module 220 and the first structural component 230, and the maximum action force detected by the pressure sensing module 220 is the maximum elastic force of the elastic module 231. The maximum elastic force is controlled within a bearable pressure range of the pressure sensing module 220 by controlling an elastic parameter of the elastic module 231, that is, damage to the pressure sensing module 220 caused by excessive pressure may be avoided.

Optionally, in the embodiment of the present application, the elastic module 231 includes, but is not limited to a spring, and may be any other type of elastic component, which is not specifically limited by the embodiment of the present application here.

In some implementation manners, the elastic module 231 is only configured to provide a preset deformation displacement for the first structural component 230, and an elastic structural component of the first button 101 is still arranged below the first button 101.

Or in some other implementation manners, the elastic module 231 may also be reused as the elastic structural component of the first button 101, and the elastic displacement provided by the elastic module 231 for the first structural component 230 is the elastic displacement of the first button 101 and is used to limit the pressing travel of the first button 101. By the implementation manner, if the first button 101 has a button travel and has an elastic structural component, the elastic structural component is reused as an elastic module for preventing damage to the pressure sensing module 220 in the embodiment of the present application. On the premise of improving the reliability and the stability of the first detection part 201, the manufacturing cost of the first button 101 and the first pulse wave detection module 210 are further reduced, so that the manufacturing cost of the electronic device is reduced.

Optionally, as shown in FIG. 20, in the embodiment of the present application, the first pulse wave detection module 210 further includes: a lens 217, where the lens 217 is arranged between the first light source 212 and the cover 211 and configured to converge the optical signals of the first light source 212 to the pressing site of the user at the cover 211 so as to increase the light intensity of the optical signals at the pressing site, thereby increasing the light intensity of the optical signal pressing through the finger and improving the quality of the PPG signal.

As an example, in FIG. 20, the first pulse wave detection module 210 includes one first light source 212 and two first light detectors 213, and the lens 217 is correspondingly arranged above the one first light source 212. It may be understood that if the first pulse wave detection module 210 includes a plurality of light sources 212, the first pulse wave detection module 210 correspondingly includes a plurality of lenses 217, where the plurality of lenses 217 are arranged above the plurality of first light sources 212 respectively in a one-to-one correspondence way.

Optionally, in the embodiment of the present application, the lens 217 may be a Fresnel lens. Compared with the traditional lens, the Fresnel lens has a short focal distance, less material consumption and smaller weight and volume, and is thinner. Therefore, the Fresnel lens is adopted in the first pulse wave detection module 210, so that more optical signals can be transmitted, the quality of the optical signals can be improved to improve the accuracy of detecting biological characteristic parameters, the thickness of the device can be compressed and the cost of the device can be reduced.

In the above embodiments, the detection apparatus for biological characteristic information 200 includes a first detection part 201. The first detection part 201 is configured to detect the pressure signal pressed by the user and the first pulse wave signal corresponding to the pressure signal, and detect the first biological characteristic information of the user according to the pressure signal and the first pulse wave signal.

In the following embodiments, the detection apparatus for biological characteristic information 200 not only includes the first detection part 201, but also includes a second detection part 202, where the second detection part 202 may be configured to detect second biological characteristic information of the user.

Optionally, in some implementation manners, the second biological characteristic information and the above first biological characteristic information may be the same type of biological characteristic information, for example, blood pressure information. The same type of biological characteristic information acquired by the two detection parts is configured to jointly determine target biological characteristic information of the user and may improve the accuracy of detecting the biological characteristic information.

Optionally, in some other implementation manners, the second biological characteristic information and the above first biological characteristic information may be different types of biological characteristic information, for example, the first biological characteristic information is blood pressure information and the second biological characteristic information is blood oxygen information, so that various biological characteristic information detection services are provided for the user and the user experience is improved.

Figure 21:
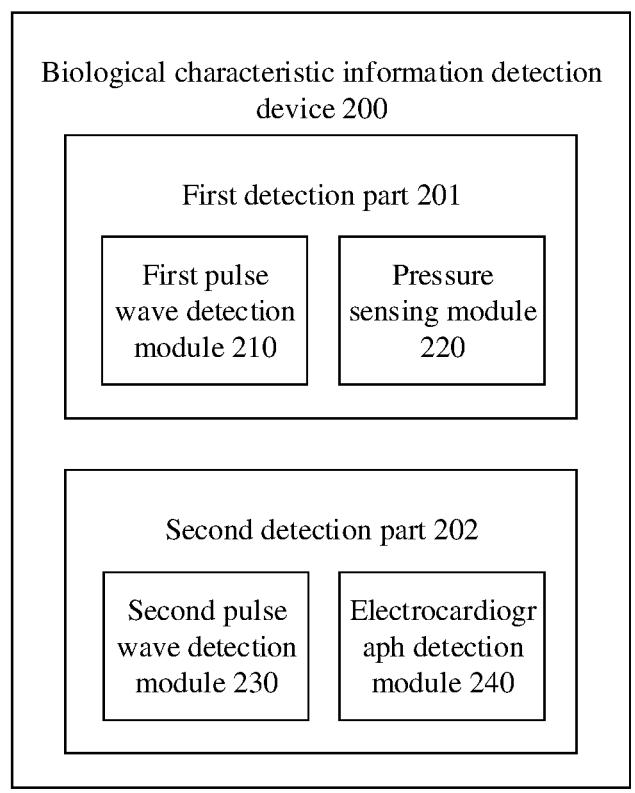
FIG. 21 is another schematic structural block diagram of a detection apparatus for biological characteristic information according to an embodiment of the present application.

FIG. 21 is schematic structural block diagram of another detection apparatus for biological characteristic information 200.

As shown in FIG. 21, the detection apparatus 200 further includes: a second detection part 202.

The second detection part 202 includes: a second pulse wave detection module 230, configured to detect a second pulse wave signal, where the second pulse wave signal is used to detect second biological characteristic information of the user; and the second biological characteristic information and the above first biological characteristic information are used for being processed to obtain target biological characteristic information of the user.

Optionally, as shown in FIG. 21, the second detection part 202 further includes: an ECG detection module 240, configured to detect an ECG signal, where the second pulse wave signal and the ECG signal are used to jointly detect the second biological characteristic information of the user.

Optionally, in the embodiment of the present application, the detection apparatus 200 further includes: a processor, connected to the first detection part 201 and the second detection part 202.

The processor is configured to acquire the first biological characteristic information of the user and the second biological characteristic information of the user. Further, the processor is configured to acquire the target biological characteristic information of the user according to the processing of the first biological characteristic information and the second biological characteristic information.

Optionally, in some possible implementation manners, the first biological characteristic information includes blood pressure calibrating information, the second biological characteristic information includes an initial blood pressure of the user, and the target biological characteristic information of the user includes a target blood pressure of the user. The processor is configured to calibrate the initial blood pressure according to the blood pressure calibrating information and take the calibrated blood pressure as the target blood pressure of the user.

In the technical solution of the embodiment of the present application, the detection apparatus may be configured to detect the blood pressure of a user, where the second pulse wave signal detected by the second detection part is a pulse wave signal detected when no pressure acts on the body surface of the user, and the accuracy of an initial blood pressure obtained based on the second pulse wave signal is low. At this time, calibration can be performed without an external auxiliary device such as a sphygmomanometer, blood pressure calibrating information is determined directly according to the first pulse wave signal and the pressure signal measured by the first detection part, the blood pressure calibrating information is provided to the initial blood pressure, the initial blood pressure is calibrated by the blood pressure calibrating information to obtain a more accurate calibrated blood pressure, and the more accurate calibrated blood pressure as the current target blood pressure of the user is fed back to the user; therefore, the detection apparatus provided by the embodiment of the present application does not need the assistance of other additional devices, is convenient to carry and can obtain a more accurate blood pressure detection result. In addition, if the blood pressure value is determined only depending on the first pulse wave signal and the pressure signal, the pressure signal needs to act on the user every time the blood pressure is detected, which is cumbersome to operate and causes a bad experience for the user. However, in the embodiment of the present application, the previously processed blood pressure calibrating information may be acquired to calibrate the initial blood pressure currently obtained according to the second pulse wave signal, so there is no need for a pressure signal to act on the user every time the blood pressure is detected, and the pressure signal and the first pulse wave signal are detected, so that the convenience of blood pressure detection and the user experience are improved while the accuracy of blood pressure detection can be further enhanced.

In some possible implementation manners, the processor is configured to: control a prompt module to output a prompt signal, the prompt signal being used to prompt the user to press the first button to form the pressure signal; control the first pulse wave detection module to detect the first pulse wave signal; control the pressure sensing module to detect the pressure signal; and receive the pressure signal and the first pulse wave signal and determine the blood pressure calibrating information according to the pressure signal and the first pulse wave signal.

Optionally, the prompt signal includes, but is not limited to one or more of a character signal, an image signal, a sound signal, a vibration signal or an optical signal, and is intended to interact with users. Correspondingly, in order to control the prompt module to output the different types of prompt signals, the detection apparatus or the electronic device where the detection apparatus is located may include different types of prompt modules.

For example, after receiving the prompt signal, the user applies a pressure to the first button to form a pressure signal. At this time, the processor controls the first pulse wave detection module in the first detection part 201 to detect the first pulse wave signal when the pressure signal acts on the user and controls the pressure detection module in the first detection part 201 to detect the pressure signal.

Then, the processor receives the first pulse signal transmitted by the first pulse wave detection module and the pressure transmitted by the pressure detection module, and determines the blood pressure calibrating information according to the pressure signal and the first pulse wave signal.

Optionally, the above prompt signal is an image signal or a video signal and may show a specific pressing mode to the user. For example, at least part of function modules in the detection apparatus, such as the first pulse wave detection module, is arranged on a side of a smartwatch, and the prompt signal may prompt the user to press in the pressing mode shown in FIG. 14, where the index finger of the user presses one side of the watch, the thumb presses the other side of the watch, the first pulse wave detection module may be arranged below the thumb or the index finger, and the pressing stability can be improved by the pressing mode, so that the detection precision of the pressure signal and the detection precision of the first pulse wave signal are improved.

Optionally, the prompt signal may also be configured to prompt the user to apply a pressure, for example, increase the applied pressure or reduce the applied pressure. After the user receives the prompt signal, the pressing force is adjusted with time change. For example, a pressure is applied to the first button with a small pressing force firstly and then the pressing force is increases gradually. For another example, the pressure is applied to the first button with a larger pressing force firstly and then the pressing force is gradually reduced. Or the pressing force may be changed in any other way, which is not specifically limited by the embodiment of the present application.

Further, when the pressing force of the user's finger changes, the pressure acting on the user's finger changes with time, and the volume of blood in the blood vessels in the finger also changes with time, so the waveform of the first pulse wave signal changes with time, and the first pulse wave signal corresponds to different pressure signals.

In some possible implementation manners, the first pulse wave signal changes with the magnitude of the pressure signal. The processor is configured to: sequence the first pulse wave signal according to the magnitude of the pressure signal to form an envelope signal of the first pulse wave signal; determine a first blood pressure of the user according to the envelope signal; and take the first blood pressure as the blood pressure calibrating information.

In the implementation manner of the present application, the first pulse wave signals corresponding to different pressures are arranged according to the sequence of the pressure signals from large to small or the sequence from small to large to form envelope signals of the first pulse wave signals. The envelope signal of the first pulse wave signal formed according to the sequence of the pressure signals may accurately reflect a relation between the amplitude of the pulse wave signals and the change of the pressure signals. Compared with the envelope signal acquired by other modes, the envelope signal formed in this mode has high signal quality, and the blood pressure detected by the envelope signals has high accuracy.

As an embodiment, the first blood pressure of the user may be determined according to the waveform parameter of the envelope signal and a preset functional equation. For example, the current diastolic pressure and systolic pressure of the user are determined, and the first blood pressure may directly serve as the blood pressure calibrating information. Optionally, the preset functional equation may be a functional equation determined according to multiple groups of experimental data, so that the reliability of calculating the blood pressure through the functional equation and the waveform parameter of the envelope signal.

In some possible implementation manners, the processor is configured to: control the second pulse wave detection module to detect the second pulse wave signal of the user; and receive the second pulse wave signal and process the second pulse wave signal by a pulse wave analysis method or a pulse wave transit time measurement method to obtain the initial blood pressure of the user.

In an implementation manner of the present application, the second pulse wave signal may be processed by the above PTT measurement method or PWA analysis method to obtain the initial blood pressure of the user, or the initial blood pressure of the user may be obtained according to the second pulse wave signal by other related art methods, which is not specifically limited by the embodiment of the present application.

Specifically, if the blood pressure is measured by the PTT measurement method, it is also necessary to measure the ECG signal corresponding to the second pulse wave signal, and the PTT is determined according to the ECG signal and the second pulse wave signal, so that the alternating current component of the current blood pressure of the user is determined, namely the initial blood pressure.

In some possible implementation manners, the processor is configured to: take the blood pressure calibrating information as a direct current component of the blood pressure of the user and take the initial blood pressure as the alternating current component of the blood pressure of the user; and calibrate the alternating current component of the blood pressure of the user according to the direct current component of the blood pressure of the user and take the calibrated blood pressure as the target blood pressure of the user.

In the implementation manner, the blood pressure calibrating information acquired by the processor may be the first blood pressure, the first blood pressure serves as the direct current component of the current blood pressure of the user, the initial blood pressure serves as the alternating current component of the current blood pressure of the user, and the current blood pressure of the user is determined according to the first blood pressure and the initial blood pressure and is output and fed back to the user.

Or in some other implementation manners, the blood pressure is calculated by the functional equation in the process of processing the second pulse wave signal by the above PTT measurement method or the PWA analysis method. According to the above blood pressure calibrating information, for example, the first blood pressure, a functional equation parameter is calibrated in the process of processing the second pulse wave signal, so that the initial blood pressure calculated according to the second pulse wave signal and the calibrated functional equation is close to, even equal to the first blood pressure, and the first blood pressure or the initial blood pressure, serving as the current blood pressure of the user, is output and fed back to the user.

The blood pressure tested by this mode is accurate, long-term and continuous blood pressure measurement can be realized, and the user experience can be improved.

In addition, it should be noted that in the embodiment of the present application, on the basis of determining the blood pressure calibrating information, in the subsequent blood pressure detection process and before each blood pressure detection, the processor firstly judges whether to update the calibration at present, new blood pressure calibrating information is acquired again if the calibration is updated, and the new blood pressure calibrating information is acquired by processing the first pulse wave signal when the pressure signal acts on the user again and the re-applied pressure signal. In addition, a new second pulse wave signal is acquired again when no pressure acts on the user, a new initial blood pressure is determined, the new initial blood pressure is calibrated in combination with the new blood pressure calibrating information, and a new blood pressure of the user is determined. If the calibration is not updated, the previous blood pressure calibrating information is directly called to acquire a new second pulse wave signal when no pressure acts on the user, and after a new initial blood pressure is determined, the new initial blood pressure is calibrated directly based on the previous blood pressure calibrating information, and a new blood pressure of the user is determined.

As an implementation manner, whether to calibrate may be judged according to first information before the blood pressure calibrating information is acquired, where the first information includes, but is not limited to: current time information and/or user input information.

Specifically, if the first information is the current time information, whether the current time information is within a preset time range is determined. If the current time information is within the preset time range, calibration is performed; otherwise, if the time information is not within the preset time range, calibration is not performed.

As an example, the preset time range may be a time period preset by a user, for example, the same time period of each month, or a time period of each day, or any other preset time period. Time information is the current time information. Whether the current time is within a preset time period is judged so as to judge whether to calibrate the detection apparatus.

Specifically, if the first information is the user input information, the user input information is used to indicate whether the user needs to calibrate the detection apparatus, and the detection apparatus is calibrated according to the requirements of the user.

Optionally, in the embodiment of the present application, the blood pressure of the user may be continuously detected by taking the preset time period as a period. Every time the blood pressure of the user is detected, whether to calibrate may be determined flexibly according to the first information, for example, the current time information and/or user input information, that is, whether to acquire new blood pressure calibrating information is determined. On one hand, the calibrating information can be updated according to the requirements of the user or regularly at the calibrating time period of blood pressure detection, and the accuracy of blood pressure detection is improved; and on the other hand, the user experience can be taken into consideration, long-term and continuous blood pressure detection is performed on the basis of the previous calibrating information and the PPG signal acquired by continuous detection at the non-calibrating time period of the blood pressure detection, and a long-term blood pressure detection service is provided.

It may be understood that the processor may be an independent processor included in the detection apparatus 200, or may also be a processor in an electronic device where the detection apparatus 200 is located. In addition to being configured to process related data detected by the detection apparatus 200, the processor may also be configured to process other data in the electronic device and perform other related functions. Optionally, the processor may be a processor 120 in the electronic device 100 in FIG. 1.

Optionally, in the embodiment of the present application, the first detection part 201 and the second detection part 202 are both configured to detect the same type of biological characteristic information of the user.

As an example, the first detection part 201 is configured to detect a first blood pressure parameter of the user, the second detection part 202 is configured to detect a second blood pressure parameter of the user, and the first blood pressure parameter and the second blood pressure parameter are configured to jointly determine a target blood pressure parameter of the user, so that the accuracy of blood pressure detection is improved.

Optionally, in some implementation manners, the above second pulse wave detection module 230 may be a second photo plethysmography (PPG) detection module. The second PPG module includes: a second light source and a second light detector, where the second light source and the second light detector may be arranged on a back of an electronic device.

Further, the above ECG detection module 240 includes: a plurality of ECG detection electrodes, where the plurality of ECG detection electrodes may be arranged on the back of the electronic device; or a first ECG detection electrode of the plurality of ECG detection electrodes is arranged on the back of the electronic device, and a second ECG detection electrode of the plurality of ECG detection electrodes is arranged on a side of the electronic device.

In the embodiment of the present application, the second light source and the second light detector in the above second PPG detection module may be correspondingly arranged on a back of a smartwatch to detect a PPG signal at a wrist continuously for a long time, so that the user may detect biological characteristic information conveniently. In addition, the first ECG detection electrode of the plurality of ECG detection electrodes is arranged on the back of the electronic device, the second ECG detection electrode of the plurality of ECG detection electrodes is arranged on the side of the electronic device, and the ECG signal at the wrist of the user and the ECG signal at the finger of the user may be detected correspondingly, so that the accuracy of detecting the biological characteristic information can be improved.

Figure 22:
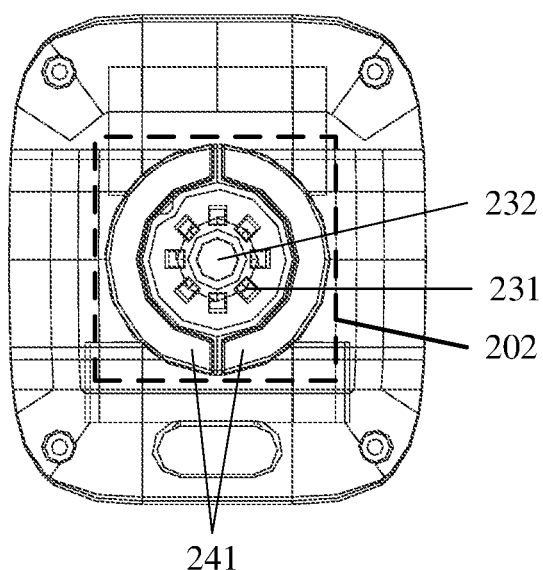
FIG. 22 is a schematic bottom view of an electronic device according to an embodiment of the present application.
Figure 23:
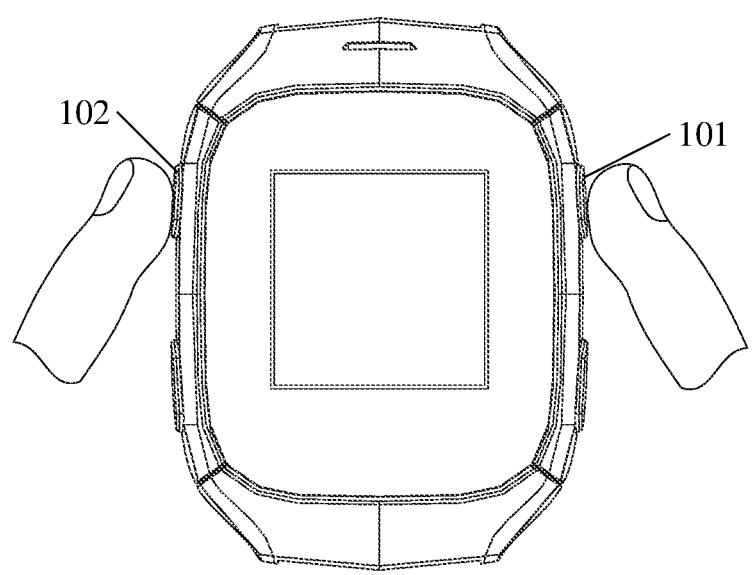
FIG. 23 is a schematic top view of the electronic device in FIG. 22.

As an example, FIG. 22 and FIG. 23 show a bottom view and a top view of an electronic device, that is, a back and a front side of the electronic device.

As shown in FIG. 22 and FIG. 23, the electronic device according to the embodiment of the present application is a smartwatch, where as shown in FIG. 22, in the second detection part 202, the second light source 231 and the second light detector 232 in the second PPG detection module 230 are both arranged in a middle area of the back of the smartwatch. When the user wears the smartwatch, the second light source 231 and the second light detector 232 face towards the wrist of the user and detect the PPG signal at the wrist of the user.

Optionally, the second PPG detection module 230 may further include a plurality of second light sources 231 and/or a plurality of second light detectors 232. As an example, as shown in FIG. 22, the plurality of light sources 231 are arranged around the second light detector 232 so as to provide an optical signal with sufficient intensity to a surface of the wrist of the user, and the second light detector 232 can receive the optical signal with sufficient intensity reflected or transmitted by the user so as to improve the detection precision of the PPG signal.

Specifically, functions of the second light source 231 and the second light detector 232 are the same as the functions of the first light source 212 and the first light detector 213 above. The related technical solutions of the second light source 231 and the second light detector 232 may be referenced to the above related description, which will not be described in detail here. Further, as shown in FIG. 22, the first ECG detection electrode 241 in the ECG detection module 240 is arranged on the back of the smartwatch and is configured to be in contact with skin of the wrist of the user so as to detect the ECG signal of the user.

On this basis, as shown in FIG. 23, the second ECG detection electrode in the ECG detection module 240 is arranged on the side of the smartwatch. Optionally, the second ECG detection electrode may be arranged on a surface of a second button 102 on the side of the smartwatch. Or the second ECG electrode may also be directly arranged on the side of the smartwatch and does not need to be arranged in a button shape.

Optionally, in the embodiment of the present application, the first detection part 201 may be arranged on a first side of the electronic device. If the first detection part 201 is arranged in the first button 101, the first button 101 may be arranged on the first side of the electronic device, the second ECG detection electrode may be arranged on a second side of the electronic device, and the first side and the second side are two opposite sides of the electronic device respectively.

As an example, as shown in FIG. 23, when the finger of the user presses the smartwatch in a way shown in FIG. 14, the index finger of the user presses the first button 101 and the thumb presses the second button 102 where the second ECG detection electrode is located. In a general application scene, the smartwatch may be worn on the wrist of the left hand of the user. In this scene, for convenience for the user to press, the first button 101 may be arranged on a button on a surface of a right side of the watch, and the second button 102 may be arranged on a button on a surface of a left side of the watch. However, if the electronic device does not include the first button which is provided with the first detection part 201 in the embodiment of the present application, the second ECG detection electrode or the second button 102 where the second ECG detection electrode is arranged on a button of a surface of a right side of the watch instead of a button on a surface of a left side of the watch.

In the embodiment of the present application, the user presses in this way. At the index finger side, the first detection part 201 at the first button 101 detects a relatively stable pressure signal and acquires a first pulse wave signal with excellent quality. Meanwhile, at the thumb side, the second ECG electrode at the second button 102 and the first ECG electrode 241 on the back of the watch may detect ECG signals at the same time. The first detection part 201 and the second detection part 202 may acquire a plurality of biological characteristic signals in one pressing process of the user's finger so as to comprehensively detect relatively accurate biological characteristic information; moreover, the structure is convenient for the user to operate so as to improve the convenience of biological characteristic detection and user experience.

Optionally, in the above embodiments of the present application, the ECG signals detected by the second ECG electrode and the first ECG electrode 241 and the PPG signal detected by the second PPG detection module are jointly used to detect biological characteristic information, such as blood pressure, of the user. In some other implementation manners, the ECG signals detected by the second ECG electrode and the first ECG electrode 241 may be independently used to detect biological characteristic information, such as heart rate, of the user.

Of course, in the above embodiments of the present application, the second detection part 202 may include the second pulse wave detection module 230 and the ECG detection module 240, or may only include the ECG detection module 240 or may only include the second pulse wave detection module 230, or may further include other biological characteristic detection modules, for example, a body temperature detection module, a heart rate detection module or a blood oxygen detection module, which is not specifically limited by the embodiments of the present application.

The embodiment of the present application further provides an electronic device. The electronic device may include the detection apparatus for biological characteristic information in any of the above application embodiments.

The electronic device includes, but is not limited to a smartwatch or smartphone, and may be specifically any electronic device shown in FIG. 1. The detection apparatus provided by the present application is convenient to carry, has high detection accuracy and is arranged in a watch and a mobile phone, so the user may conveniently realize blood pressure detection anytime and anywhere through the mobile phone or watch carried by the user, so that the blood pressure detection is no longer limited to a medical device, and the blood pressure detection can be better popularized and serve people's daily life.

It should be understood that specific examples in the embodiments of the present application are only intended to help those skilled in the art to better understand the embodiments of the present application and do not limit the embodiments of the present application.

It should also be understood that various implementation manners described in this specification may be implemented alone or in combination, which is not limited by the embodiments of the present application.

Unless otherwise stated, all technical and scientific terms used in the embodiments of the present application have the same meaning as those commonly understood by those skilled in the technical field of the present application. The terms used in the present application are only for the purpose of describing the specific embodiments and are not intended to limit the scope of the present application. The term "and/or" used in the present application includes any and all combinations of one or more of associated listed items. As used in the embodiments of the present application and the appended claims, the singular forms "a", "above" and "the" are intended to include the plural forms, unless the context clearly indicates other meanings.

Those of ordinary skill in the art may realize that the units of each example described in the embodiments disclosed herein can be realized in electronic hardware, computer software or a combination of the two. In order to clearly describe the interchangeability of hardware and software, the composition and steps of each example have been generally described in the above description according to functions. Whether these functions are implemented in hardware or software depends on specific applications of the technical solutions and design constraints. Those skilled in the art may use different methods to implement the described functions for each specific application, but such implementation should not be considered to be beyond the scope of the present application.

In several embodiments provided by the present application, it should be understood that the disclosed system and device may be implemented in other manners. For example, the described device embodiment is merely exemplary. For example, the unit division is merely logical function division and may be other division in actual implementation. For example, a plurality of units or components may be combined or integrated into another system, or some features may be ignored or not performed. In addition, the displayed or discussed mutual coupling or direct coupling or communication connection may be indirect coupling or communication connection through some interfaces, devices or units, or may be electrical connection, mechanical connection or connection in other forms.

The units described as separate parts may or may not be physically separate. Parts displayed as units may or may not be physical units, which may be located at one position, or may be distributed on a plurality of network units. Some or all of the units may be selected according to actual needs to achieve the objectives of the solutions of the embodiments of the present application.

In addition, various functional units in each embodiment of the present disclosure may be integrated into one processor, or each of the units may exist alone physically, or two or more units may be integrated into one unit. The foregoing integrated unit may be implemented either in the form of hardware or in the form of software functional units.

The integrated unit, if implemented in the form of a software functional unit and sold or used as a stand-alone product, may be stored in a computer readable storage medium. Based on this understanding, the technical solution of the application is essentially or the part that contributes to the prior art or all or part of the technical solution may be embodied in the form of a software product. The computer software product is stored in a storage medium, including several instructions for enabling one computer device (may be a personal computer, a server or a network device) to perform all or part of steps of the method in each embodiment. The aforementioned storage medium includes various mediums that may store a program code, such as a USB flash drive, a mobile hard disk, a read-only memory (ROM), a random access memory (RAM), a magnetic disk, or an optical disk.

The above is only a specific embodiment of the present application, but the protection scope of the present application is not limited to this. Various equivalent modifications or substitutions which may be easily thought by those skilled in the art in the technical scope disclosed by the present application should be covered within the protection scope of the present application. Therefore, the protection scope of the present application should be subject to the protection scope of the claims.

What is claimed is:

1. An electronic device, comprising:
    a first button, wherein a cavity is formed in a shell of the first button,
    a detection apparatus comprising a first detection part, wherein the first detection part comprises:
    a first pulse wave detection module at least partially arranged in the cavity of the first button and configured to detect a first pulse wave signal of a user when the user presses the first button, wherein the first pulse wave detection module is a first photo plethysmography (PPG) detection module which comprises a first light source and a first light detector; and
    a pressure sensing module at least partially arranged in the cavity of the first button and configured to detect a pressure signal applied to the first button by the user, the first pulse wave signal being a corresponding pulse wave signal when the user applies the pressure signal, wherein the pressure sensing module is a pressure sensor;
    the electronic device further comprising:
    a processor configured to detect first biological characteristic information of the user according to the pressure signal and the first pulse wave signal;
    wherein the first pulse wave detection module is fixedly connected to the shell of the first button, and the pressure sensing module is fixedly connected to the first pulse wave detection module;
    the first detection part further comprises: a first structural component arranged on one side, facing towards the inside of the electronic device, of the pressure sensing module;
    when the user presses the first button, the pressure sensing module and the first pulse wave detection module are configured to press the first structural component in a linkage way;
    the pressure sensing module is configured to detect an action force between the pressure sensing module and the first structural component so as to detect the pressure signal applied to the first button by the user;
    the first detection part further comprises: an elastic module arranged on one side, facing towards the inside of the electronic device, of the first structural component and connected to the first structural component, wherein the elastic module comprises a spring;
    when the user presses the first button, the first structural component, the pressure sensing module and the first pulse wave detection module are configured to press the elastic module in a linkage way; and
    the elastic module is configured to limit a movable distance of the pressure sensing module within a preset range so as to limit a force applied by the user within a pressure range bearable by the pressure sensing module.

2. The electronic device according to claim 1, wherein the pressure sensing module and the first pulse wave detection module are stacked, and the pressure module is located on one side, facing towards the inside of the electronic device, of the first pulse wave detection module.

3. The electronic device according to claim 2, wherein the first pulse wave detection module is fixedly connected to the shell of the first button, and the pressure sensing module is separably arranged on one side of the first pulse wave detection module;

the first detection part further comprises: a second structural component fixedly connected to one side, facing towards the inside of the electronic device, of the first pulse wave detection module, wherein the second structural component and the pressure sensing module are arranged on the same side of the first pulse wave detection module;

when the user presses the first button, the second structural component and the first pulse wave detection module are configured to press the pressure sensing module in a linkage way; and the pressure sensing module is configured to detect an action force between the pressure sensing module and the second structural component so as to detect the pressure signal.

4. The electronic device according to claim 1, wherein the elastic module is used as an elastic structural component of the first button, and the elastic module is configured to limit a pressing stroke of the first button.

5. The electronic device according to claim 1, wherein the first PPG detection module comprises: a light-transmitting cover, the first light source and the first light detector; the light-transmitting cover being configured to receive pressing of the user, the first light source and the first light detector being arranged on one side, facing towards the inside of the electronic device, of the light-transmitting cover, the first light source being configured to transmit an optical signal of a target waveband to a pressing site of the user at the light-transmitting cover, and the first light detector being configured to receive an optical signal reflected and/or transmitted by the pressing site to form the first pulse wave signal; and the light-transmitting cover is part of the shell of the first button.

6. The electronic device according to claim 5, wherein first PPG detection module further comprises: a substrate and a bracket, the substrate being configured to support the first light source and the first light detector, and the bracket being arranged on a peripheral edge of the substrate and configured to support the light-transmitting cover; and the light-transmitting cover, the bracket and the substrate are formed as a closed chamber.

7. The electronic device according to claim 6, wherein the bracket and/or the substrate is part of the shell of the first button.

8. The electronic device according to claim 1, wherein the first button is arranged on a side or a back of the electronic device.

9. The detection apparatus according to claim 1, wherein the first button is a function button of the electronic device.

10. The electronic device according to claim 1, further comprising: a second detection part, wherein the second detection part comprises:
a second pulse wave detection module configured to detect a second pulse wave signal of the user, the second pulse wave signal being used to detect second biological characteristic information of the user, wherein the second pulse wave detection module is a second photo plethysmography (PPG) detection module which comprises a second light source and a second light detector, and the processor further configured to process the first biological characteristic information and the second biological characteristic information to obtain a target biological characteristic information of the user.

11. The electronic device according to claim 10, wherein the second detection part further comprises: an electrocardiogram (ECG) detection module configured to detect an ECG signal of the user, the ECG signal and the second pulse wave signal being used to detect the second characteristic biological information of the user; and the second PPG detection module being arranged on a back of the electronic device; and the ECG detection module comprises: a plurality of ECG detection electrodes, a first ECG detection electrode of the plurality of ECG detection electrodes being arranged on a back of the electronic device, and a second ECG detection electrode of the plurality of ECG detection electrodes being arranged on a side of the electronic device.

12. The electronic device according to claim 11, wherein the first button is arranged on a first side of the electronic device, the second ECG detection electrode is arranged on a second side of the electronic device, and the first side and the second side are two opposite sides of the electronic device respectively.

13. The electronic device according to claim 12, wherein the second ECG detection electrode is arranged in a second button on a side of the electronic device.

14. The electronic device according to claim 10, wherein the processor is connected to the first detection part and the second detection part, the processor is configured to acquire the first biological characteristic information of the user, acquire the second biological characteristic information of the user, and process the first biological characteristic information and the second biological characteristic information to obtain the target biological characteristic information of the use; and the processor is configured to obtain blood pressure calibrating information of the user according to the pressure signal and the first pulse wave signal, obtain an initial blood pressure of the user according to the second pulse wave signal, calibrate the initial blood pressure according to the blood pressure calibrating information and take the calibrated blood pressure as a target pressure of the user.

15. The electronic device according to claim 14, wherein the processor is configured to: control the second pulse wave detection module to detect the second pulse wave signal of the user; and receive the second pulse wave signal and process the second pulse wave signal by a pulse wave analysis method or a pulse wave transit time measurement method to obtain the initial blood pressure of the user.

16. The electronic device according to claim 14, wherein the first pulse wave signal is variable with the magnitude of the pressure signal; and the processor is configured to: sequence the first pulse wave signal according to the magnitude of the pressure signal and form an envelope signal of the first pulse wave signal, determine a first blood pressure of the user according to the envelope signal, and take the first blood pressure as the blood pressure calibrating information.

* * * * *